United States Patent
Ohkawa et al.

(10) Patent No.: US 6,613,961 B1
(45) Date of Patent: Sep. 2, 2003

(54) PLANTS CAPABLE OF METABOLIZING DRUGS AND USE THEREOF

(75) Inventors: Hideo Ohkawa, Hyogo (JP); Yasunobu Ohkawa, Ibaraki (JP); Kenjirou Ozawa, Ibaraki (JP); Sakiko Hirose, Saitama (JP)

(73) Assignees: Bio-Oriented Technology Research Advancement Institution (JP); National Institute of Agrobiological Sciences (JP)

( * ) Notice: Subject to any disclaimer, the term of this patent is extended or adjusted under 35 U.S.C. 154(b) by 0 days.

(21) Appl. No.: 09/787,593

(22) PCT Filed: Mar. 26, 1999

(86) PCT No.: PCT/JP99/01573

§ 371 (c)(1),
(2), (4) Date: Jun. 22, 2001

(87) PCT Pub. No.: WO00/17352

PCT Pub. Date: Mar. 30, 2000

(30) Foreign Application Priority Data

Sep. 21, 1998 (JP) .......................... 10/266513

(51) Int. Cl.[7] .................. C12N 5/10; C12N 15/82; C12N 15/12; A01H 5/00; C02F 3/32
(52) U.S. Cl. ................. 800/300; 47/58.1; 424/93.7; 435/418; 435/419; 800/288; 800/317; 800/320; 800/298; 800/278
(58) Field of Search ................. 536/23.1, 23.4, 536/23.5; 435/418, 419; 800/300, 317, 278, 320, 288, 298; 47/58.1; 424/93.7

(56) References Cited

PUBLICATIONS

Gray et al., A 2,4–Megabase Physical Map Spanning the CYP2C Gene Cluster on Chromosome 10q24, 1995, Genomics, vol. 28, pp. 328–332.*

Shiota et al., Herbicide–Resistant Tobacco Plants Expessing the Fused Enzyme beteween . . . , 1994, Plant Physiol, vol. 106, pp. 17–23.*

Shiota, N. et al. "Herbicide–Resistant Tobacco Plants Expressing the Fused Enzyme Between Rat Cytochrome P4501A1 (CYP1A1) and Yeast NADPH–Cytochrome P450 Oxidoreductase" *Plant Physiol.* (1994) pp. 17–23, 106(1).

Shiota, N. et al. "Metabolism of the Herbicide Chlortoluron in Transgenic Tabacco Plants Expressing the Fused Enzyme Between Rat Cytochrome P4501A1 and Yeast NADPH–Cytochrome P450 Oxidoreductase" *Pesticide Biochemistry and Physiology* (1996) pp. 190–198, 54(3).

Hirose, S. et al. "Evaluation of Herbicide Resistance in the P450 Transgenic Rice Mediated by *Agrobacterium*" *Breeding Science* (1998) p. 176, vol. 48, Supp. 1.

Inui, H. et al. "Cross–Tolerance of Transgenic Potato Plants Co–Expressing Xenobiotic–MetabolizinogHuman CYP1A1, CYP2B6 and CYP2C19" *Breeding Science* (1998), p. 127, vol. 48, Supp. 2.

Inui, H. et al. "Herbicide Metabolism and Cross–Tolerance in Transgenic Potato Plants Expressing Human CYP1A1" *Pesticide Biochemistry and Physiology* (1999) pp. 33–46, vol. 64.

Ohkawa, H. et al. "Molecular Mechanisms of Herbicide Resistance with Special Emphasis on Cytochrome P450 Monooxygenases" *Plant Biotechnology* (1998) pp. 173–176, vol. 15, No. 4.

Imai, Y. et al. "P450–Sono Tayouna Kinou to Ouyou" *Protein, Nucleic Acid and Enzyme* (1998) pp. 203–215, 43(3).

* cited by examiner

Primary Examiner—David T. Fox
Assistant Examiner—David H. Kruse
(74) Attorney, Agent, or Firm—Saliwanchik, Lloyd & Saliwanchik

(57) ABSTRACT

Transgenic plants capable of metabolizing drugs are constructed by introducing a drug-metabolizing P450 molecular species into plants. These plants are capable of detoxifying and metabolizing foreign compounds such as environmental loads and extrinsic endocrine disruptors including drugs, poisons, and agrochemicals. Thus, they are highly useful when applied to field crops, etc. Also, a method for selecting the drug-metabolizing P450 molecular species is provided.

9 Claims, 18 Drawing Sheets

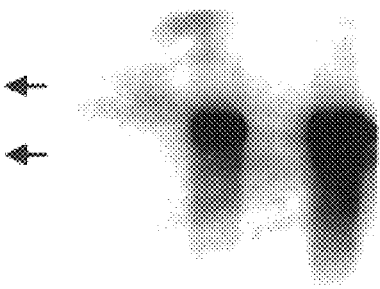
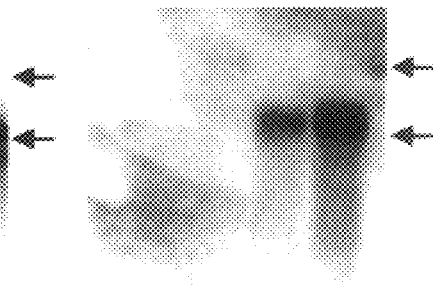
1 2 3 4 5  1 2 3 4 5  1 2 3 4 5
FIG. 14A   FIG. 14B   FIG. 14C

1  2  3  4  5

1  2  3  4  5

1  2  3  4  5

1  2  3  4  5

1  2

PLANTS CAPABLE OF METABOLIZING DRUGS AND USE THEREOF

This application is the National Stage of International Application No. PCT/JP99/01573, filed Mar. 26, 1999.

TECHNICAL FIELD

The present invention relates to transgenic plants on which capability of metabolizing, for example, drugs is conferred and use thereof.

BACKGROUND ART

Industrial development and advancement has increased kinds of environmental loads which destroy ecosystem. Moreover, numerous substances which disturb reproduction mechanism of organisms with an extremely small amount, such as extrinsic endocrine disruptors, have been reported. Environmental loads, extrinsic endocrine disruptors, and such are concentrated in the body of living organisms and more concentrated through food chain to profoundly affect living organisms and ecosystem. Therefore, it is necessary not only to remove these substances from environment, but also to metabolize and detoxify these in living organisms which have incorporated these substances.

Especially, plants are organisms belonging to the bottom of food chain, and plants in which these substances accumulate can be a source of destroying ecosystem. Thus, metabolizing and detoxifying these substances in plants are very important subjects.

Regarding agricultural crops which are closely related to our diet, agrochemicals such as herbicides, which are environmental loads, are generally used for cultivation. Thus, detoxifying residual agrochemicals in agricultural crops is needed for preventing adverse effect on humans and livestock which ingest these chemicals.

Cytochrome P450 monooxygenase (abbreviated to "P450" hereinafter) is an enzyme which distributes in a broad range of living organisms from microorganisms to plants and mammals and has a role of metabolizing and detoxifying drugs incorporated into living organisms. For P450 to exert its activity, another enzyme which provides p450 with electrons (abbreviated to "P450 reductase" hereinafter), for example, NADPH-P450 reductase, is required. This enzyme is also present in a broad spectrum of living organisms. The present inventors have created artificial enzymes showing extremely high oxidation activity by constructing fusion enzymegenes of various P450 molecular species and P450 reductases (Unexamined Published Japanese Patent Application (JP-A) No. Sho 63-44888, JP-A Hei 2-23870, and JP-A Hei 2-249488).

Recently, P450 in plants has been studied and various P450 molecular species broadly present in plants have been revealed. An activity of many drug-metabolizing P450 molecular species present in plants is, however, low, and capability of metabolizing environmental loads is extremely weak. Therefore, a novel plant with an enhanced capability of metabolizing environmental loads and such has been needed to create.

Specifically, it has been necessary to provide field crops which are used directly for foods and for feed and which play an important role in human life with the capability of metabolizing and detoxifying environmental loads and extrinsic endocrine disruptors represented by agrochemicals.

DISCLOSURE OF THE INVENTION

The present inventors have earnestly studied under these circumstances and successfully created transgenic plants on which capability of metabolizing, for example, drugs is conferred, by expressing drug-metabolizing P450 molecular species of mammals in plants. Transgenic plants of the present invention have the capability of metabolizing various herbicides depending on a molecular species of P450 expressed by them, and thus, show tolerance to these herbicides. Especially, an individual in which multiple P450 molecular species have been expressed can show higher tolerance to a broad spectrum of herbicides by the synergistic effect. Due to such a characteristic, the transgenic plants of the present invention are very useful as herbicide-tolerance plants. Moreover, these can absorb, metabolize, and decompose herbicides dispersed in the soil and, thus, are extremely environment-friendly. In addition, these plants can be used as a phytoremediation plant which can defecate environment by utilizing a plant (by using light energy) to metabolize and decompose not only herbicides but also environmental loads and extrinsic endocrine disruptors.

Therefore, the present invention provides transgenic plants which express a mono-oxygen addition activity derived from P450 or express a fusion enzyme activity comprising both mono-oxygen addition activity derived from P450 and reducing power-providing ability derived from P450 reductases and which can metabolize and decompose environmental loads and extrinsic endocrine disruptors, and use thereof.

Specifically, the present invention provides:
(1) a DNA molecule functionally comprising (a) a promoter capable of functioning in plant cells, (b) a P450 monooxygenase gene, and (c) a terminator capable of functioning in plant cells,
(2) the DNA molecule of (1), wherein the P450 monooxygenase gene is a fusion gene with a P450 reductase gene,
(3) the DNA molecule of (1) or (2), wherein the P450 monooxygenase gene is a gene belonging to CYP2 family,
(4) the DNA molecule of (3), wherein the gene belonging to CYP2 family is a gene selected from the group consisting of CYP2B6, CYP2C9, CYP2C18, and CYP2C19 genes,
(5) the DNA molecule of any one of (1) to (4), wherein the P450 monooxygenase gene is derived from mammals,
(6) a transgenic plant cell into which the DNA molecule of any one of (1) to (5) has been introduced,
(7) the transgenic plant cell of (6), wherein more than one type of P450 monooxygenase genes has been introduced into the transgenic plant cell,
(8) a transgenic plant comprising the plant cell of (6) or (7),
(9) the transgenic plant of (8), wherein the transgenic plant is a gramineous plant or a solanaceous plant,
(10) the transgenic plant of (8) or (9), wherein the transgenic plant is capable of decomposing a foreign compound by the oxidative metabolism,
(11) the transgenic plant of (10), wherein a foreign compound is an environmental load or an extrinsic endocrine disrupter,
(12) the transgenic plant of (10) or (11), wherein the transgenic plant comprises herbicide tolerance,
(13) a propagation material of the plant of any one of (8) to (12),
(14) a method for removing a foreign compound in environment, wherein the transgenic plant of (10) or (11) is used, and
(15) a method for selecting a P450 monooxygenase capable of metabolizing herbicides or a gene thereof, the method comprising:
(a) preparing a microsomal fraction from each transformant expressing one type of P450 monooxygenase gene introduced respectively into each transformant, (b) reacting the microsomal fraction with an active ingredient of a herbicide, (c) detecting a parent compound (the active ingredient of the herbicide) and/or a reaction product (a metabolite of the active ingredient of the herbicide), and (d) selecting the P450 monooxygenase for which the reduction of the amount of the parent compound and/or the production of the reaction product has been detected, or a gene thereof.

In the present invention "environmental loads" mean substances which are released to the environment and provide loads to the ecosystem. "Extrinsic endocrine disruptors" mean substances which are present out of living organisms and cause hormone-like effect when incorporated into living organisms.

Any P450 molecular species can be used herein as long as they have a mono-oxygen addition activity, but those derived from mammals, which comprise higher activity than those derived from plants, are preferable. In this specification, "a mono-oxygen addition activity" means an activity catalyzing a reaction which adds a single oxygen atom to a substrate molecule. P450 molecular species belonging to CYP1, 2, 3, and 4 families are known to be mainly involved in the oxidative metabolism of foreign compounds, such as environmental loads including drugs, toxins, and agrochemicals, and thus, can be preferably used for the present invention (Imai, Y., and Kamataki, T., Protein, Nucleic acid and Enzyme, 1998, 43, 203–215). Specifically a preferable molecular species belonging to CYP1 family is derived from humans, for example, human CYP1A1 and human CYP1A2.

A herbicide metabolized by each P450 molecular species can be determined, for example, by preparing a microsomal fraction from a transformant in which each P450 molecule is expressed, by reacting the microsomal fraction with an active ingredient of each herbicide, and then, by detecting and analyzing a parent compound (an active ingredient of a herbicide) or a reaction product (a metabolite of the active ingredient in the herbicide).

Specifically, a P450 monooxygenase capable of metabolizing herbicides or the gene thereof can be selected by a method comprising:

(a) preparing a microsomal fraction from each transformant expressing one type of P450 monooxygenase gene introduced respectively into each transformant, (b) reacting the microsomal fraction with an active ingredient of a herbicide, (c) detecting a parent compound (the active ingredient of the herbicide) and/or a reaction product (a metabolite of the active ingredient of the herbicide), and (d) selecting the P450 monooxygenase for which the reduction of the amount of the parent compound and/or the production of the reaction product has been detected, or the gene thereof.

Any types of P450 monooxygenase genes can be used for the selection as long as they have a mono-oxygen addition activity, but those derived from mammals are preferable because they can be expected to have higher herbicide-metabolizing ability compared with those derived from plants. A P450 mononxygenase gene can be introduced into, for example, yeast, insect cells, plant cells, and so on but not limited to them.

A microsomal fraction can be prepared by the various methods known to a person skilled in the art. An example is the method described in "Oeda, K. et al., DNA, 1985, 4, 203–210" for yeast. Recombinant yeast strain microsomal fractions which express each molecular species of human P450 are available in the market (for example, Sumitomo Chemical).

Any herbicides can be used for a reaction. For example, the triazine compounds such as atrazine; the urea compounds such as chlorotoluron, diuron, and methabenzthiazuron; the diazine compounds such as norflurazon; the pyrimidinyloxybenzene compounds such as pyriminobacmethyl; the acetanilide compounds such as acetochlor, alachlor, and metolachlor; the dinitroaniline compounds such as triflurarin; the benzofuranylalkanesulfonate compounds such as benfuresate and ethofumesate; the sulfonylurea compounds such as chlorosulfuron and imazosulfuron; and the carbamate compounds such as pyributicarb can be used, but not limited thereto.

A microsomal fraction is reacted with an active ingredient of a herbicide by suspending the microsomal fraction in phosphate buffer at around pH 7 so that the amount of a P450 in the microsomal fraction is constant, and adding (i) NADPH for donating an electron to a P450 through a P450 reductase, (ii) a substrate and an enzyme for reproducing NADPH from NADP produced by donation of an electron (for example, glucose-6-phosphate and glucose-6-phosphate dehydrogenase), and (iii) a herbicide (a concentration depends on a type of herbicides). The reaction was carried out in a range of temperature suitable for an organism from which a p450 molecular species is derived (for example, 37° C. for human P450), by mixing with air while vigorously shaking, within a period during which an enzyme is not inactivated (for example, for 10 to 60 min).

A parent compound (an active ingredient of a herbicide) or a reaction product (a metabolite of the active ingredient of the herbicide) can be detected and analyzed by, for example, the liquid chromatography (LC) and the liquid chromatography/mass spectrometry (LC/MS). If a peak of a parent compound decreases and instead a peak derived from a metabolite is confirmed, a sample used for an assay is determined to be capable of metabolizing a herbicide. From the height of the peak, a metabolized amount can be obtained.

The present inventors have been confirmed that, for example, human CYP1A1, human CYP2B6, human CYP2C18, human CYP2C19can metabolize respective herbicides below, and these can be preferably used for the present invention.

Human CYP1A1: N-deethylation, N-deisopropylation, and so on of the triazine compounds and such including atrazine; N-demethylation, ring hydroxylation, and so on of the urea compounds and such including chlorotoluron, diuron, methabenzthiazuron; N-demethylation and so on of the diazine compunds and such including norflurazon; hydroxylation and so on of the pyrimidinyloxybenzene compounds and such including pyriminobac-methyl.

Human CYP2B6: O-deethylation, O-demethylation, and so on of the acetanilide compounds and such including acetochlor, alachrol, metolachlor; O-demethylation and so on of the dinitroaniline compounds and such including triflurarin; O-deethylation, hydroxylation, and so on of the benzofuranylalkanesulfonate and such including benfuresate and ethofumesate.

Human CYP2C9: ring hydroxylation and so on of the sulfonylurea compounds and such including chlorosulfuron and imazosulfuron.

Human CYP2C18: N-demethylation, ring hydoxylation, and such of the urea compounds and such; O-deethylation, O-demethylation, and so on of the acetanilide compounds and such; O-demethylation and such of the dinitroaniline compounds and such; O-deethylation, hydroxylation, and so on of the benzofuranylalkanesulfonate compounds and such.

Human CYP2C19: N-deethylation, N-deisopropylation, and so on of the triazine compounds and such; N-demethylation, ring hydroxylation, and so on of the urea compounds and such; N-demethylation and so on of the diazine compounds and such; O-deethylation, O-demethylation, and so on of acetanilide compounds and such; thioester cleavage and so on of the carbamate compounds and such including pyributicarb; O-demethylation and so on of pyrimidinyloxybenzene compounds and such.

In the present invention, more than one type of P450 genes can be simultaneously expressed in a plant, and thereby, a capability of metabolizing a range of compounds broader than the case of expressing single P450 gene can be provided for a plant. Even when a plant does not show herbicide resistance due to its weak metabolizing capability from single P450 gene expression alone, herbicide tolerance can be provided for a plant by expressing more than one type of P450 genes to improve the metabolizing capability.

Any P450 reductases can be used in the present invention as long as they have a reducing power-providing activity to transfer an electron to a P450. For example, NADH-P450 reductases derived from microorganisms such as bacteria, NADPH-P450 reductases derived from mammals or plants, and so on can be used (Takemori, S., and Kominami, S., Cytochrome P-450, University of Tokyo Press).

In the present invention, a P450 can be solely expressed in a plant or with a P450 reductase which donates an electron to the P450. A P450 reductase can be expressed as a fusion protein with a P450. For constructing a fusion gene of a P450 gene and a P450 reductase gene, refer to the publications (JP-A Sho 63-44888, JP-A Hei 2-23870, and JP-A Hei 2-249488).

To express a gene in a plant cell, a DNA molecule (an expression cassette) functionally comprising (1) a promoter capable of functioning in plant cells, (2) the gene, and (3) a terminator capable of functioning in plant cells is prepared and introduced into the plant cells. Such a DNA molecule can contain a DNA sequence for improving transcription other than a promoter, for example, an enhancer sequence. Any promoters can be used as long as they function in plant cells. Examples are 35S (Schell, J. S., Science, 1987, 237, 1176–1183), Nos (Schell, J. S., Science, 1987, 237, 1176–1183), rbcS (Benefy, P. N., and N-H. Chua, Science, 1989, 244, 174–181), PR1a (Ohshima, M. et al., Plant Cell, 1990, 2, 95–106), ADH (Benefy, P. N. and N-H. Chua, Science, 1989, 244, 174–181), patatin (Benefy, P. N., and N-H. Chua, Science, 1989, 244, 174–181), Cab (Benefy, P. N., and N-H. Chua, Science, 1989, 244, 174–181), and PAL (Liang, X. et al., Proc. Natl. Acad. Sci. USA, 1989, 86, 9284–9288). Such DNA molecules contain various vectors for expressing a gene.

A gene can be introduced into plant cells by the various methods known to a person skilled in the art. For example, indirect introduction methods using *Agrobacterium tumefaciens* or *Agrobacterium rhizogenes* (Hiei, Y. et al., Plant. J., 1994, 6, 271–282; Takaiwa, F. et al., Plant Sci., 1995, 111, 39–49) or direct introduction methods represented by electroporation method (Tada, Y. et al., Theor. Appl. Genet, 1990, 80, 475), a polyethylene glycol method (Datta, S. K., et al., Plant Mol Biol., 1992, 20, 619–629), and a particle gun method (Christou, P. et al., Plant J., 1992, 2, 275–281; Fromm, M. E., Bio/Technology, 1990, 8, 833–839) can be used. Any "plant cells" can be used for gene introduction in the present invention as long as they are capable of regenerating an individual plant, and, for example, suspension cultured cells, calli, protoplasts, leaf slices, and so on are included.

An individual plant can be created by regenerating transformed plant cells. Plant species to be created in the present invention are not particularly limited, and, for example, gramineous plants such as rice, wheat, maize, gramineous pasture, and turf; solaneceous plants such as tobacco, tomato, and potato; crucifer crops such as rape; and plants such as sunflower and alfalfa, are especially preferable as a target plant on which capability of metabolizing drugs and such is conferred. Methods for regenerating an individual plant depend on a species of plant cells. Representative methods are, for example, the method by Fujimura et al. for rice (Fujimura, T. et al., Plant Tissue Culture. Lett., 1995, 2, 74), the methods described in the references (Akbar, S. et al., Plant Cell, Tissue and Organ Culture, 1991, 26, 185–187; Altpeter, F. et al., Plant Cell Rep., 1996, 16, 12–17) for wheat, the methods described in the references (Singh, R. R., et al., Plant Cell, Tissue and Organ Culture, 1997, 49, 121–127) for barley, the method described by Armstrong et al. (Armstrong, C. L. and Phillips, R. L., Crop Sci. , 1988, 28, 363–369) for maize, the method described in the reference (Dalton, S. J., Biotechnology in Agriculture and Forestry, 1993, 22, 46–68) for Italian rye grass, the method described in the reference (Asano, Y., Plant Cell Rep., 1989, 8, 141–143) for turf, the method described in the reference (Rogers, S. G. et al., Methods Enzymol., 1986, 118, 627–640) for tobacco, the method described in the reference (Sheerman, S and Bevan, M. W., Plant Cell Rep., 1988, 7, 13–16) for potato, the method described in the reference (Kohno-Murase, J. et al., Plant Mol. Biol., 1994, 26, 1115–1124) for rape, the method described in the reference (Schrammeijer, B. et al., Plant Cell Rep., 1990, 9, 55–60) for sunflower, and the method described in the reference (Shahin, E. A. et al., Crop Sci., 1986, 26, 1235–1239) for alfalfa.

An individual plant created in the present invention or that created from propagation materials (for example, seeds, tuberous roots, tubers, fruits, ear, etc.) thereof is capable of oxidatively metabolizing and detoxifying foreign compounds, for example, environmental loads and extrinsic endocrine disruptors including drugs, toxins, and agrochemicals.

More tolerant individuals can be selected by examining tolerance to one or more herbicides in the obtained transgenic plants. Preferably, the function of an introduced gene in a selected individual is confirmed by assaying introduction of a target P450 cDNA into chromosomal DNA, production of mRNA, production of a P450 protein corresponding to the introduced gene, a P450 enzyme activity, etc.

Specific examples of drugs and toxins to be oxidatively metabolized and detoxified by the individual plants of the present invention are, for example, benzopyrene and such for CYP1A1 (Shimada, T. et al., Cancer Res., 1991, 49, 6304–6312), nicotine and such for CYP2B6 (Flammang, A. M. et al., Biochem. Arch., 1992, 8, 1–8), Ibuprofen (Leeman, T. et al., 1993, Life Sci., 52: 29–34), Tolbutamide (Brian, W. R. et al., 1989, Biochemistry, 28: 4993–4999), and such for CYP2C9, Tolbutamide and such for CYP2C18 (Furuya, H., Mol. Pharmacol. 1991, 40, 375–382), Mephenytoin (Shimada, T. et al., 1986, J. Biol. Chem., 261: 909–921), Omeprazol (Anderson T. et al., 1990, Ther. Drug Monitoring, 12: 415–416), and such for CYP2C19, but not limited thereto.

Examples of agrochemicals are the acetanilide or dinitroaniline herbicides and the like, such as alachlor (Monsanto etc.), metolachlor (former Ciba-Geigy, Novartis, etc.), triflurarin (Eli Lilly etc.), and acetochlor (Monsanto etc.); the sulfonylurea herbicides and the like, such as chlorosulfuron (E. I. du pont de Nemous and Co. Inc. etc.) and imazosulfuron (Takeda Chemical industries, Ltd., etc.); the carbamate herbicides and the like, such as pyributicarb (Toso, etc.); the triazine herbicides and the like, such as simazine (former Chiba-Geigy, Novartis, etc.) and atrazine (former Geigy, Novartis, etc.); the diazine herbicide and the like, such as norflurazon (former Santos, Novartis, etc.); the urea herbicides and the like, such as chlorotoluron (former Chiba, Novartis, etc.) and methabenzthiazuron (Bayer etc.); but not limited thereto.

Therefore, environmental loads can be reduced or tolerance to the compounds can be provided by directly or indirectly contacting the plants of the present invention with these foreign compounds. Moreover, accumulation of the foreign compounds in vivo or residual agrochemicals can be reduced.

In developing countries and such, appropriate water management is difficult in most paddy fields, and control of weeds is cumbersome in these paddies. Rice plants capable of metabolizing drugs created in the present invention acquire resistance to herbicides by metabolizing the herbicides. Cultivating these rice plants makes control of weeds efficient without increasing loads to environmental. Similarly, these rice plants are effective for controlling weeds at the early stage in direct sowing fields.

In addition, parasitic plants such as Orobanche (Japanese name Hamautsubo) and Cuscuta (Japanese name Hamanenashikazura) parasitize various crops such as tobacco, tomato, potato, sunflower, and alfalfa. So far, there is no herbicide which can distinguish between parasitic plants and host plants. By introducing P450 genes such as CYP2C9, into hosts, parasitic plants can be controlled by a small amount of drugs.

(A) indicates western blot analyses using anti-human CYP1A1 antibody. A sample in each lane is as follows.
  Lane 1, microsomal fraction of recombinant yeast strain which expressed human CYP1A1.
  Lane 2, microsomal fraction of S1965;
  Lane 3, microsomal fraction of S1972;
  Lane 4, microsomal fraction of S1974;
  Lane 5, microsomal fraction of non-transformed plants;
  Lane 6, microsomal fraction of T1979;
  Lane 7, microsomal fraction of T1977;
  Lane 8, microsomal fraction of T1978.

(B) shows Western blot analyses using anti-human CYP2B6 antibody. Lane 1 shows a result for microsomal fraction of a recombinant yeast strain which expressed human CYP2B6, and lanes 2 to 8 show results for the same samples as those of (A) above.

(C) shows Western blot analyses using anti-human CYP2C9 antibody. Lane 1 shows a result for microsomal fraction of a recombinant yeast strain which expressed human CYP2C19, and lanes 2 to 8 show results for the same samples as those of (A) above.

Figure 13A:
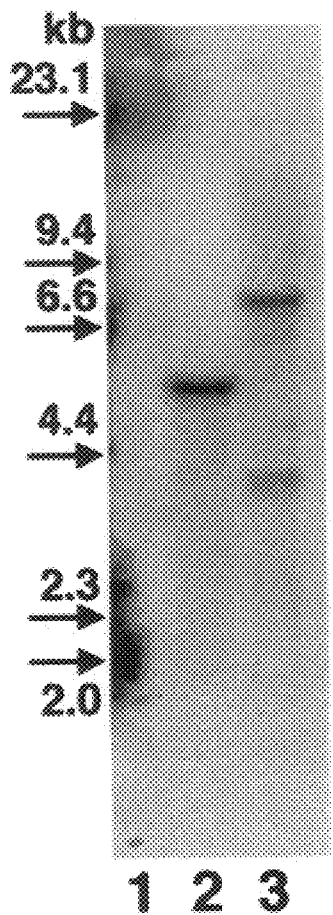
Figure 13B:
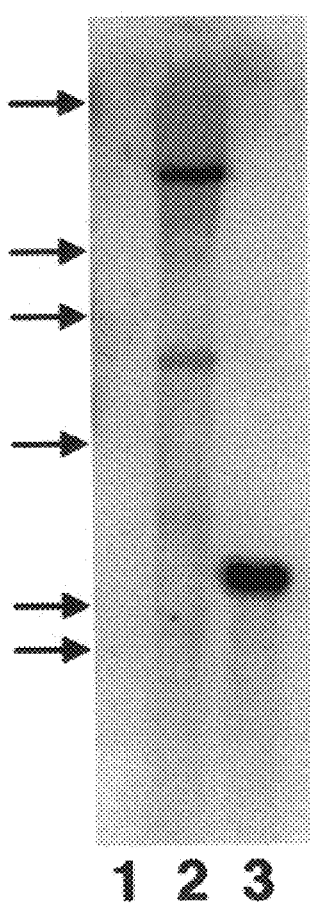
Figure 13C:
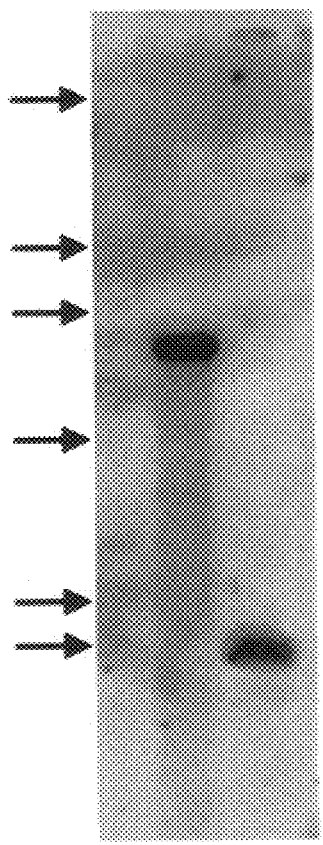

FIG. 13 shows Southern blot analyses for transformants.
  Human CYP1A1 probe was used for (A). Lanes 1, 2, and 3 show results for non-transformed plants, T1977, and S1965, respectively.
  Human CYP2B6 probe was used for (B). Lanes 1, 2, and 3 show results for non-transformed plants, T1977, and S1972, respectively.

Human CYP2C19 probe was used for (C). Lanes 1, 2, and 3 show results for non-transformed plants, T1977, and S1974, respectively.

FIG. 14 shows Northern blot analyses for transformants.

Human CYP1A1 probe was used for (A). Lanes 1, 2, 3, 4, and 5 show results for non-transformed plants, S1965, S1972, S1974, and T1977, respectively.

Human CYP2B6 probe was used for (B). Lanes 1 to 5 show results for the same sample as those of (A).

Human CYP2C19 probe was used for (C). Lanes 1 to 5 show results for the same sample as those of (A).

Figure 15A:
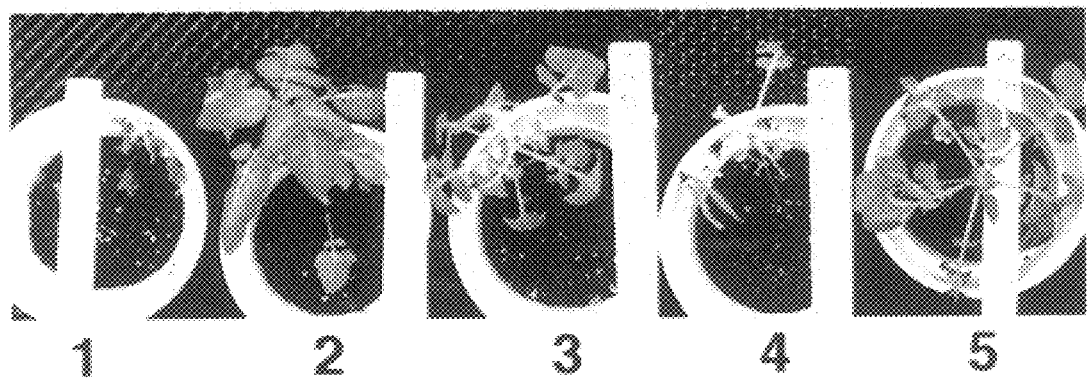
Figure 15B:
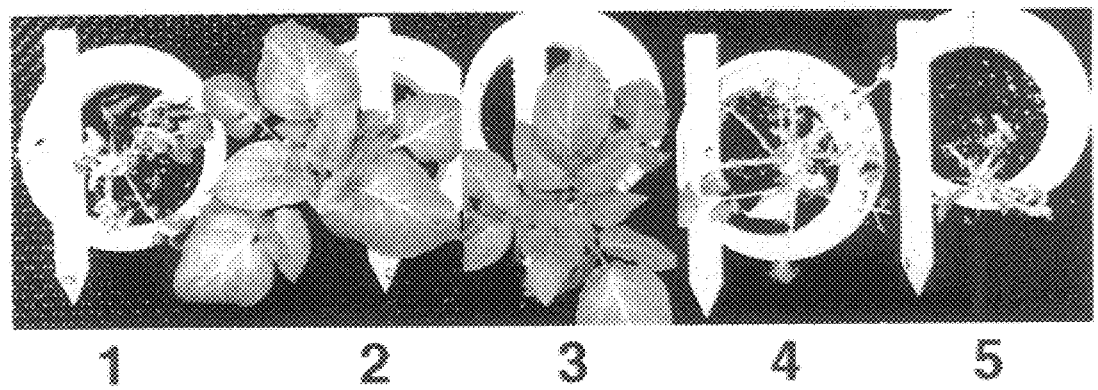
Figure 15C:
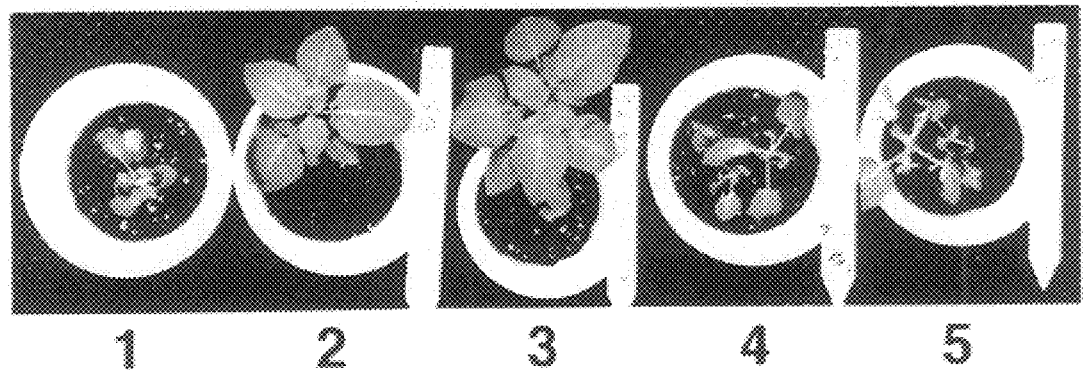

FIG. 15 shows assays for tolerance of transformants to photosynthesis-inhibiting herbicides.

(A) shows results of the herbicide atrazine dispersal assays. Lanes 1, 2, 3, 4, and 5 are results for non-transformed plants, T1977, S1965, S1972, and S1974, respectively.

(B) shows results of the herbicide chlorotoluron dispersal assays. Lanes 1 to 5 show results for the same sample as those of (A).

(C) shows the results of the herbicide methabenzthiazuron dispersal assays. Lanes 1 to 5 show results for the same sample as those of (A).

Figure 16A:
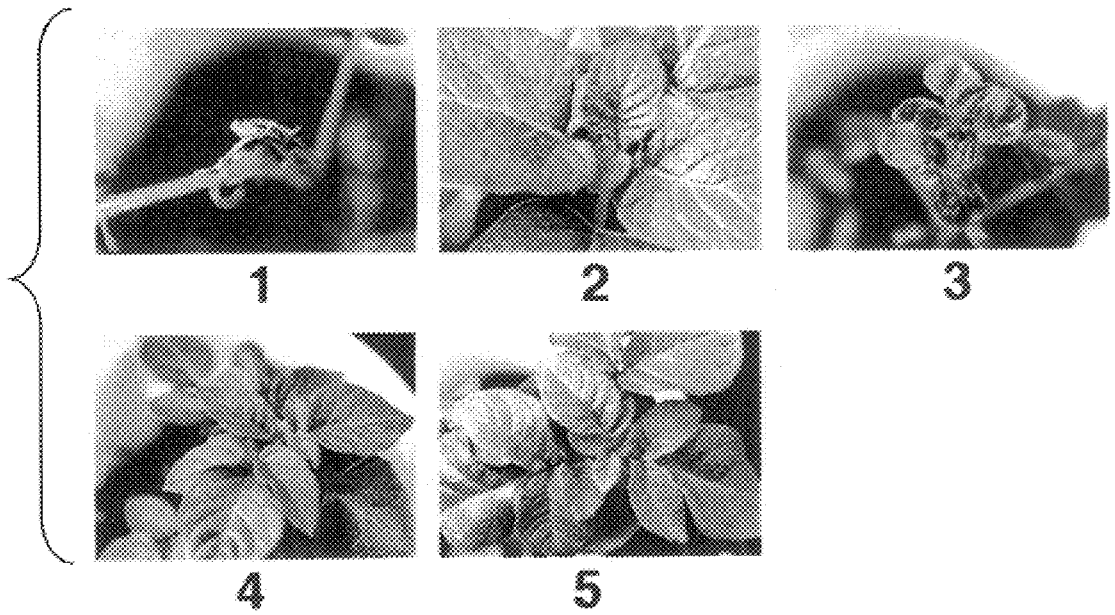
Figure 16B:
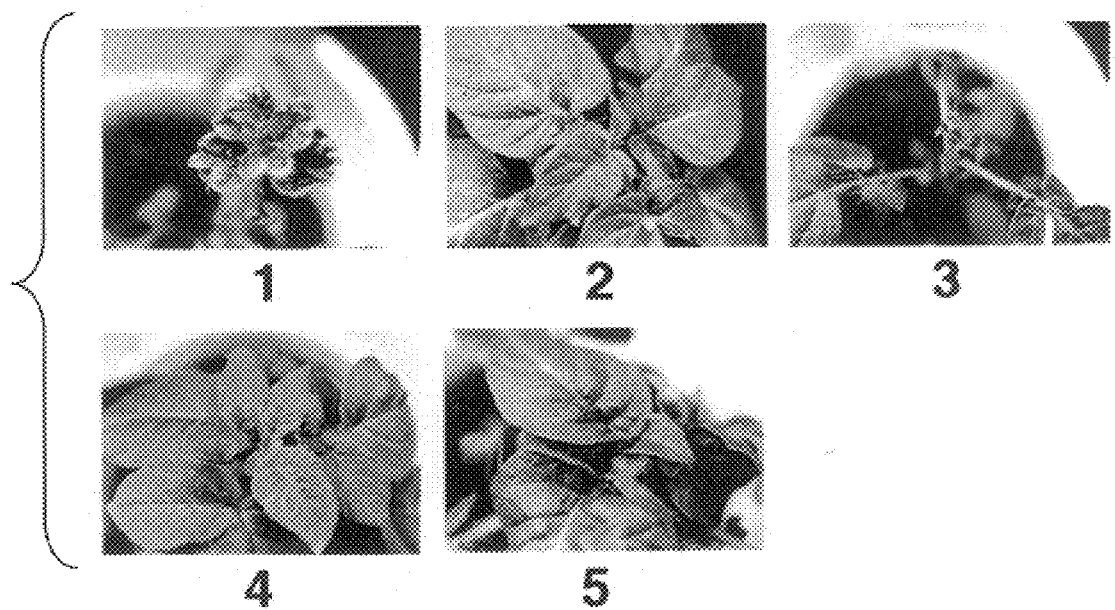

FIG. 16 shows assays for tolerance of transformants to protein synthesis-inhibiting herbicides.

(A) shows results of the herbicide acetochlor dispersal assays Lanes 1, 2, 3, 4, and 5 are results for non-transformed plants, T1977, S1965, S1972, and S1974, respectively.

(B) shows results of the herbicide metolachlor dispersal assays. Lanes 1 to 5 show results for the same sample as those of (A).

Figure 17:
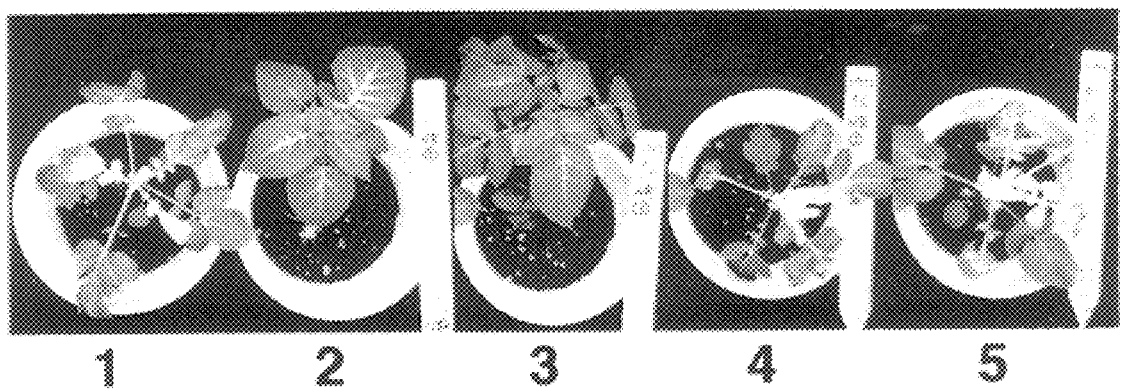

FIG. 17 shows assays for tolerance of transformants to carotenoid biosynthesis-inhibiting herbicide norflurazon. Lanes 1, 2, 3, 4, and 5 are results for non-transformed plants, T1977, S1965, S1972, and S1974, respectively.

Figure 18A:
Figure 18B:
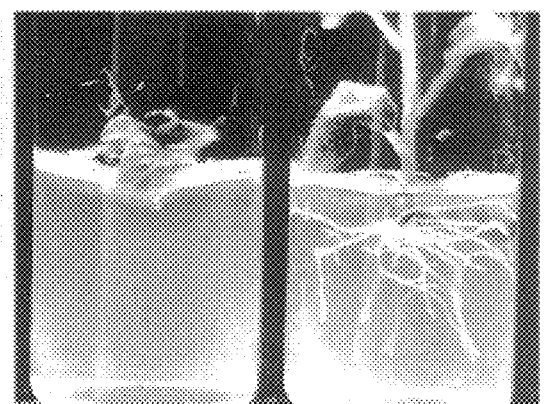

FIG. 18 shows assays for tolerance of transformants to lipid biosynthesis-inhibiting herbicide pyributicarb.

(A) Lanes 1, 2, 3, 4, and5 are results for non-transformed plants, T1977, S1965, S1972, and S1974, respectively.

(B) shows the magnified figures for lanes 1 and 2.

BEST MODE FOR CARRYING OUT THE INVENTION

The present invention is illustrated by Examples in detail below, but not limited to the following Examples, and the ordinal modification in the art of the present invention can be carried out.

EXAMPLE 1

Construction of Binary Plasmid pIJ2B6

Figure 1:
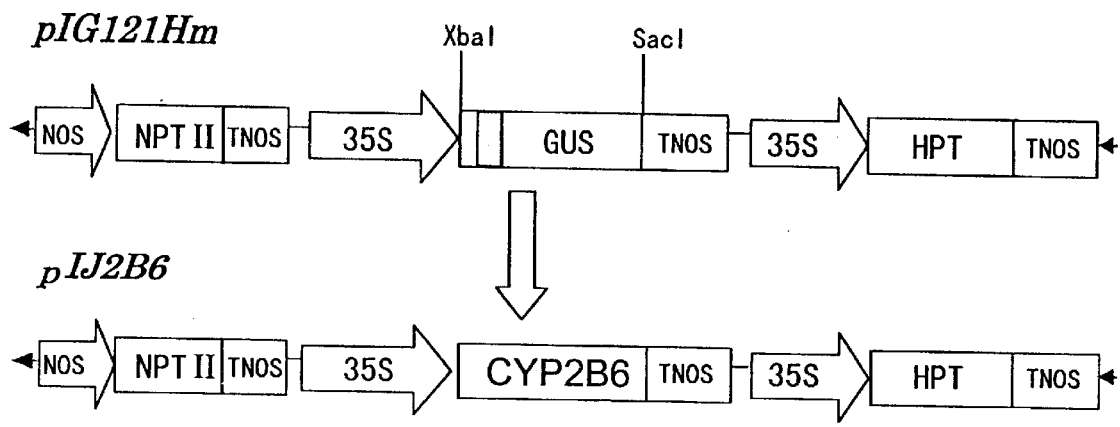
FIG. 1 schematically shows the construction of binary plasmid pIJ2B6. NOS, Nos promoter; NPT II, kanamycin resistance gene; TNOS, Nos terminator; 35S, cauliflower mosaic virus 35S promoter; HPT, hygromycin resistance gene; GUS, β-glucuronidase gene.

FIG. 1 shows the constructed binary plasmid pIJ2B6. The region encoding human CYP2B6 was excised from pUCA2B6 (Imaoka, S. et al., Biochem. Pharmacol., 1996, 51, 1041–1050) with Xba I and Sac I and inserted into binary vector pIG121Hm (Ohta, S. et al., Plant Cell Physiol., 1990, 31, 805–813, a gift from Dr. Nakamura, K. of Nagoya University) from which the intron GUS gene was removed by digestion with Xba I and Sac I to construct pIJ2B6 plasmid vector, which was expressed by the cauliflower mosaic virus 35S promoter (35S-P).

EXAMPLE 2

Introduction of Binary Plasmids into Agrobacterium

The constructed plasmid pIJ2B6 was introduced into *Agrobacterium tumefaciens* strain EHA101 (Hood, E. E. et al., J. Bacteriol., 1986, 168, 1291–1301) by electroporation using a cuvette (BTX) with 2 mm width under the condition of 129 Ω, 2.5 kV, and 50 μF (Electro Cell Manipulator 600, BTX). Agrobacteria containing this binary vector were selected on the LB agar medium with 50 μg/ml kanamycin and 50 μg/ml hygromycin. Plasmids prepared from the selected clones were digested by various restriction enzymes, and the presence of the plasmid was confirmed by the fragment length.

EXAMPLE 3

Infection to Rice Plants

Rice plants were infected with the agrobacterium based on the method of Hiei, et al. in 1994 (Hiei Y. et al., Plant J., 1994, 6, 271–282). Mature rice seeds (Nipponbare) were threshed, sterilized, and cultured on the N6D solid medium containing 2,4-D (Toki, S., Plant Mol. Biol. Rep., 1997, 15, 16–21) for 2 to 3 weeks to obtain calli derived from scutellum. These calli were infected with the agrobacterium transformed by the method of Example 2, co-cultured on the 2N6AS solid medium (Toki, S., Plant Mol. Biol. Rep., 1997, 15, 16–21) for 3 days, and sterilized with sterile water containing carbenicillin. These calli were selectively cultured on the N6D solid medium containing 50 μg/ml hygromycin and 100 μg/ml carbenicillin for 2 weeks. Proliferated calli were further selected on the same solid medium for 2 weeks and regenerated on the MS regeneration medium containing 50 μg/ml hygromycin (Toki, S., Plant Mol. Biol. Rep., 1997, 15, 16–21) to obtain transformed plants (R0).

EXAMPLE 4

Preparation of Rice Chromosomal DNA and Confirmation of a Target Gene by Southern Hybridization and PCR Chromosomal DNA was prepared from rice leaves by CTAB method (Rogers, S. O. and Bendich, A. J., Plant Molecular Biology Manual, 1988, A6, 1–10) using hexadecyltrimethylammonium bromide. About 300 mg of leaves were frozen in a mortar with liquid nitrogen, crushed with a pestle until getting powder, and subjected to extraction with 2×CTAB solution. The crude extract was extracted with phenol/chloroform, and DNAs were collected by ethanol precipitation, and suspended in TE. These chromosomal DNAs were digested with restriction enzyme Sac I, subjected to agarose gel electrophoresis, and adsorbed onto a nylon membrane. The Sac I fragment containing about 60% of the target gene (869 bp) was excised from plasmid pIJ2B6. Southern hybridization was conducted, using the above fragment as a probe, with the membrane onto which the extracted rice chromosomal DNA was adsorbed, and detection was performed using ECL nucleic acid labeling detection kit (Amersham). The introduction of the target gene into rice chromosomes was confirmed.

Moreover, to confirm the introduction of the gene in more lines, chromosomal DNA was extracted from rice leaves by a simple method, and the PCR (94° C. for 5 min and 35 cycles of 94° C., 63° C., and 72° C., for 1 min, 1 min, and 2 min, respectively) was conducted using primers which specifically annealed to human CYP2B6 gene. The target DNA was confirmed to be inserted into the chromosomal DNA in most transgenic plants.

EXAMPLE 5

Preparation of Rice Microsomal Fraction and Confirmation of Target Enzyme Expression by Western Blot Seeds were obtained from the transgenic plants (R0) and sowed to obtain R1 individuals. The target R1 individuals containing CYP2B6 gene were selected by PCR, and microsomal fractions were prepared from their leaves. Rice leaves were frozen with liquid nitrogen and crushed in a mortar, and, after addition of microsomal fraction preparation buffer (Shiota, N. et al., Plant Physiol., 1994, 106, 17–23), centrifuged at 1,000× g for 10 min twice. The supernatant was centrifuged at 100,000× g for 1 hour to obtain the microsomal fraction as a precipitate. After solubilized using a buffer containing 0.1% SDS, the fraction was subjected to the SDS-polyacrylamide electrophoresis and proteins in a gel were adsorbed onto the nitrocellulose membrane. The nitrocellulose membrane was incubated in blocking solution (PBS buffer containing 4% milk protein and 0.1% Tween20) for 1 hour, and then further incubated for 1 hour with the anti-rat CYP2B1 antibody (Gentest) (the anti-rat CYP2B1 antibody reacts with human CYP2B6) diluted to 1/3000 with the blocking solution. The nitrocellulose membrane was washed with the blocking solution three times and incubated with peroxidase-labeled anti-rabbit IgG-antibody diluted to 1/5000 with the blocking solution for 1 hour. The membrane was washed with the blocking solution twice and with the PBS buffer containing 0.1% Tween20 twice. With the membrane, an X ray film was exposed for 30 min to 1 hour using the ECL Western blotting detection kit (Amersham) to detect the band for the target protein. As a reference standard for CYP2B6 protein, a standard for human CYP2B6WB of Gentest was used. As a result, the band, reactive with the anti-rat CYP2B1 antibody, was detected at about 48 kDa in any transgenic rice plants. It was confirmed that the target enzyme was produced in the transgenic plants and localized in microsomal fraction.

EXAMPLE 6

Germination Assay for Herbicide Resistance of Rice R1 Seeds

Transgenic rice plants (R0 individuals) were grown to obtain R1 seeds. The obtained R1 seeds were sowed on hormone-free Murashige & Skoog (MS) medium containing metolachlor, alachlor, and triflurarin, which show weeding effects on gramineous plants, for examining tolerance at germination. Four grains threshed and sterilized with sodium hypochlorite solution were sowed on each 10 ml of MS solid medium containing 2.5 $\mu$M metolachlor, 2.5 $\mu$M alachlor, and 15 $\mu$M triflurarin at the final concentrations. Germination of seeds of Nipponbare into which the gene was not introduced was inhibited after about 4 to 7 days, and both shoots and roots did not elongate. On the other hand, the individuals of which shoots and roots normally elongated in the same manner as those elongated in herbicide-free medium were segregated from seeds of transgenic rice plants. Tables 1 and 2 show the results of herbicide tolerance of each line. For alachlor and triflurarin, only values for the segregated individuals which showed resistance were shown.

Values for degrees of tolerance in Table 1 or for herbicide tolerance in Table 2 indicate the following.

1, same as the control (Nipponbare);

2, slightly tolerant;

3, very tolerant;

4, same as growth without herbicide.

TABLE 1

Resistance to herbicide metolachlor at the germination of the transgenic rice plants and their segregation ratios

| Line | Digree | Tolerance | Death | Line | Digree | Tolerance | Death | Line | Digree | Tolerance | Death |
| --- | --- | --- | --- | --- | --- | --- | --- | --- | --- | --- | --- |
| A142 | 4 | 4 | 0 | A11 | 3 | 6 | 4 | A317 | 2 | 2 | 2 |
| A158 | 4 | 3 | 1 | A35 | 3 | 3 | 1 | A2153 | 2 | 2 | 2 |
| A183 | 4 | 11 | 1 | A41 | 3 | 3 | 1 | | | | |
| A186 | 4 | 10 | 5 | A156 | 3 | 2 | 2 | A22 | 1 | | |
| A234 | 4 | 3 | 1 | A178 | 3 | 3 | 1 | A120 | 1 | | |
| A262 | 4 | 3 | 1 | A181 | 3 | 19 | 7 | A148 | 1 | | |
| A294 | 4 | 3 | 1 | A187 | 3 | 2 | 2 | A159 | 1 | | |
| A299 | 4 | 30 | 3 | A217 | 3 | 1 | 3 | A160 | 1 | | |
| A355 | 4 | 3 | 1 | A218 | 3 | 3 | 1 | A161 | 1 | | |
| A1116 | 4 | 2 | 2 | A274 | 3 | 3 | 1 | A196 | 1 | | |
| A1145 | 4 | 3 | 1 | A330 | 3 | 4 | 0 | A257 | 1 | | |
| A1150 | 4 | 4 | 0 | A345 | 3 | 1 | 3 | A272 | 1 | | |
| A1180 | 4 | 3 | 1 | A371 | 3 | 3 | 1 | A290 | 1 | | |
| A1181 | 4 | 3 | 0 | A375 | 3 | 4 | 0 | A315 | 1 | | |
| A1183 | 4 | 4 | 0 | A397 | 3 | 3 | 1 | A1141 | 1 | | |
| A4117 | 4 | 2 | 2 | A424 | 3 | 2 | 2 | A1161 | 1 | | |
| A4131 | 4 | 2 | 2 | A476 | 3 | 3 | 1 | A1170 | 1 | | |
| | | | | A1113 | 3 | 10 | 6 | A2127 | 1 | | |
| | | | | A1126 | 3 | 13 | 3 | A2129 | 1 | | |
| | | | | A1127 | 3 | 2 | 2 | | | | |
| | | | | A1144 | 3 | 3 | 1 | | | | |
| | | | | A1156 | 3 | 12 | 6 | | | | |
| | | | | A1164 | 3 | 4 | 4 | | | | |
| | | | | A4137 | 3 | 4 | 0 | | | | |
| | | | | A4139 | 3 | 3 | 1 | | | | |
| | | | | A4164 | 3 | 3 | 1 | | | | |

TABLE 2

Resistance to various herbicides at the germination of the transgenic rice plants

| Line | Metolachlor | Alachlor | Triflurarin |
| --- | --- | --- | --- |
| A163 | 4 | 2 | 3 |
| A186 | 4 | 2 | 3 |

TABLE 2-continued

Resistance to various herbicides at the germination of the transgenic rice plants

| Line | Metolachlor | Alachlor | Triflurarin |
|------|-------------|----------|-------------|
| A11 | 3 | — | 3 |
| A181 | 3 | 2 | 3 |
| A1113 | 3 | 2 | 3 |
| A1126 | 3 | — | 3 |
| A1156 | 3 | — | 3 |
| A198 | 2 | 3 | 2 |
| A1161 | 1 | 1 | 1 |

EXAMPLE 7

Construction of Binary Plasmid pHU2C9

Figure 2:
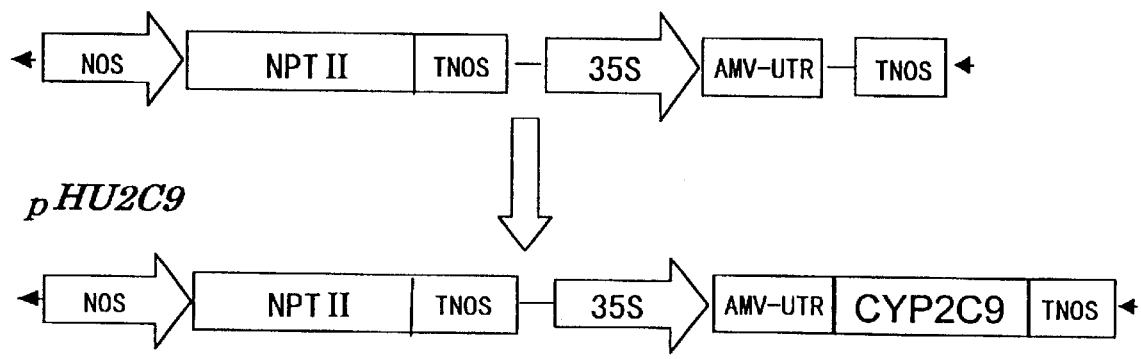
FIG. 2 schematically shows the construction of binary plasmid pHU2C9. NOS, NOS promoter; NPT II, kanamycin resistance gene; TNOS, Nos terminator; 35S, cauliflower mosaic virus 35S promoter; AMV-UTR, alfalfa mosaic virus 5' non-translational region.

FIG. 2 shows the constructed binary plasmid pHU2C9. The pHU2C9 plasmid vector, which was expressed by the cauliflower mosaic virus 35S promoter (35S-P), was constructed by inserting human CYP2C9 cleaved with Xba I and Sac I (Imaoka, S. et al., Biochem. Pharmacol., 1996, 51, 1041–1050) into the binary vector pUTR121H derived from pBI121 (Toyobo) digested with Xba I and Sac I in the same manner.

EXAMPLE 8

Introduction of Binary Plasmid into Agrobacterium

The constructed plasmid pHU2C9 was introduced into *Agrobacterium tumefaciens* strain LBA4404 (Toyobo) by freezing-thawing method. The agrobacteria containing this binary vector were selected on LB agar medium containing 50 μg/ml kanamycin. The plasmids prepared from these were digested with various restriction enzymes, and the presence of them was confirmed by the fragment length.

EXAMPLE 9

Infection to Tobacco

Tobacco plants were infected with the agrobacterium based on the method of Rogers et al. (Rogers, S. G. et al., Methods Enzymol., 1986, 118, 627–640) using leaf discs. Transformed plants (R0) were obtained by rediffrentiating on MS rediffrentiation medium containing 100 μg/ml kanamycin. The obtained R0 plants were grown on MS medium containing 50 nM chlorosulfuron, and vigorously growing individuals were selected.

EXAMPLE 10

Preparation of Tobacco Chromosomal DNA and Confirmation of the Target Gene by Southern Hybridization Chromosomal DNA was prepared from tobacco leaves using hexadecyltrimethylammonium bromide by CTAB method in the same manner as Example 4. The prepared chromosomal DNA was digested with restriction enzyme Xba I, subjected to agarose gel electrophoresis, and adsorbed onto a nylon membrane. The Xba I-Hind III fragment containing about 60% of the target gene (851 bp) was excised from plasmid pHU2C9. Southern hybridization was conducted, using the above fragment as a probe, with the membrane onto which the extracted tobacco chromosomal DNA was adsorbed, and detection was performed using ECL nucleic acid labeling detection kit (Amersham). The introduction of the target gene into tobacco chromosomes was confirmed.

EXAMPLE 11

Preparation of Tobacco Total RNA and Confirmation of mRNA of the Target Gene by Northern Hybridization Total RNA of tobacco leaves was prepared by ATA method (Nagy, F. et al., Plant Molecular Biology Manual, 1988, B4, 1–29). About 1 g of leaves were frozen with liquid nitrogen in a mortar, crushed with a pestle until getting powder, and subjected to extraction with RNA extraction buffer. The crude extract was extracted with phenol/chloroform, and RNA was collected by ethanol precipitation. Total RNA (25 μg) was subjected to 1% formaldehyde agarose gel electrophoresis and adsorbed onto a nylon membrane. Northern hybridization was conducted, using the Xba I-Sac I fragment of 2C9 gene excised from plasmid pHU2C9 as a probe, with the membrane onto which the extracted total RNA of tobacco was adsorbed. Detection was carried out with ECL nucleic acid labeling detection kit (Amersham), and mRNA expression of the target gene was confirmed in the tobacco leaves.

EXAMPLE 12

Preparation of Tobacco Microsomal Fraction and Confirmation of Target Enzyme Expression by Western Blot Individuals for which the presence of the target gene and mRNA expression were confirmed by Southern blot analysis and Northern blot analysis were selected, and a microsomal fraction was prepared using the whole proliferated cultured plants. The plants were crushed in microsomal fraction preparation buffer, and centrifuged at 1,000× g for 10 min and at 10,000× g for 20 min. $MgCl_2$ was added thereto, and the mixture was centrifuged at 4,000× g for 20 min to precipitate a microsomal fraction. This fraction was homogenized in extraction buffer (Shiota, N. et al., Plant Physiol., 1994, 106, 17–23), centrifuged at 100,000× g for 60 min, and suspended in suspension buffer (Shiota, N. et al., Plant Physiol., 1994, 106, 17–23). A microsomal protein (50 μg) was subjected to the SDS-polyacrylamide electrophoresis, and the protein in the gel was adsorbed onto PVDF membrane. The protein was detected by coloring of BCIP and NBT with the polyclonal antibody against CYP2C9 as a probe. As a result, for any transgenic tobacco plant, the band reactive with the anti-CYP2C9 antibody was detected at the position corresponding to about 56 kDa. It was confirmed that the target enzyme was produced in the transgenic tobacco plants and localized in the microsomal fraction.

EXAMPLE 13

Assay for Herbicide Resistance in the Tobacco R0 Plants

Transformed and non-transformed tobacco plants proliferated from axillary buds were transferred onto hormone-free Murashige & Skoog (MS) medium containing 0, 20, 50, 100, or 200 nM chlorosulfuron for assaying tolerance at growth. The growth of the non-transformed plants was completely inhibited by 50 nM chlorosulfuron, while the transformants grew even at the concentration of 200 nM (Table 3).

Values in the table indicate the following condition.

1, almost dead;

2, severely inhibited growth;

3, slightly inferior growth;

4, the same growth as that when the herbicide was not dispersed.

TABLE 3

Tolerance of the tobacco transformants cultured for 40 days to chlorosulfuron

| | Concentration (nM) | | | | |
|---|---|---|---|---|---|
| | 0 | 20 | 50 | 100 | 200 |
| Non-transformed | 4 | 2 | 1.5 | 1 | 0.5 |
| Only vector introduced | 4 | 2 | 1.5 | 1 | 0.5 |
| N8 | 4 | 4 | 4 | 2.5 | 2 |
| N60 | 4 | 4 | 4 | 3 | 3 |
| N61 | 4 | 4 | 4 | 2 | 2 |
| N69 | 4 | 4 | 4 | 2 | 2 |

EXAMPLE 14

Herbicide Metabolism in the Tobacco R0 Plants

Using the tobacco R0 plants 3 weeks after transplantation, metabolism of chlorosulfuron was measured by the method of Sweetser et al. (Sweetser, P. B. et al., Pestic. Biochem. Physiol., 1982, 17, 18–23). $^{14}$C-labeled 0.5 mM chlorosulfuron (20 µl) was spread on the leaf surface. The leaf surface was washed with acetone 50 hours after the treatment, and a metabolite was extracted by acetone extraction. The extract was concentrated and dried by a rotary evaporator, dissolved in methanol, and analyzed by thin layer chromatography using benzene:acetone:formic acid (30:10:1) as an solvent. As a result, there was no difference in the chlorosulfuron amount between the transformants and the non-transformed plants, but there was almost no fraction of III in the transformants, which were supposed as a metabolite in plant bodies, and water-soluble substances which remained at the starting point of the development were increased.

EXAMPLE 15

Construction of Binary Plasmid pUHC19

Figure 3:
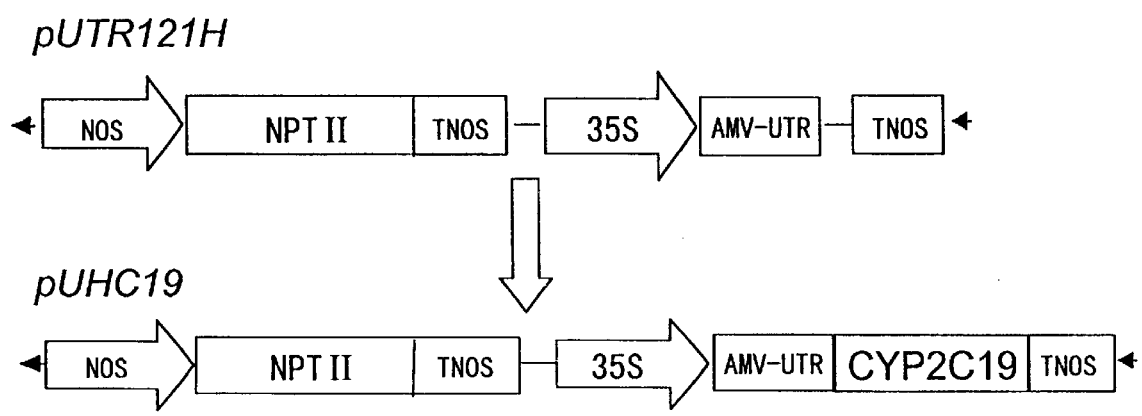
FIG. 3 schematically shows construction of binary plasmid pUHC19. NOS, Nos promoter; NPT II, kanamycin resistance gene; TNOS, Nos terminator; 35S, cauliflower mosaic virus 35S promoter; AMV-UTR, alfalfa mosaic virus 5' non-translational region.

FIG. 3 shows the constructed binary plasmid pUHC19. Human CYP2C19 (a gift from Sumitomo Chemical) excised with Hind III was inserted into pUTR121H digested with Hind III to construct pUHC19 plasmid vector, which was expressed by the cauliflower mosaic virus 35S promoter (35S-P).

EXAMPLE 16

Introduction of the Binary Plasmid into Agrobacterium

The constructed plasmid pURC19 was introduced into *Agrobacterium tumefaciens* strain LBA4404 (Hoekema, A. et al., Nature, 1983, 303, 179–180) by electroporation (Electro Cell Manipulator 600, BTX) using a cuvette (BTX) with 2 mm width under the condition of 129 Ω, 2.5 kV, and 50 µF. The agrobacteria containing this binary vector were selected on LB agar medium containing 50 µg/ml kanamycin. The plasmids prepared from the selected agrobacteria were digested various restriction enzymes, and the presence of the plasmid was confirmed by the fragment length.

EXAMPLE 17

Infection to Potato Plants and Obtaining the Transformants

Potatoes were infected with the agrobacterium based on the method of Ishige et al. (Ishige, T. et al., Plant Science, 1991, 73, 167–174) using microtuber discs. Transformants were obtained by redifferentiation on 3C5ZR redifferentiation medium containing 100 µg/ml kanamycin (Sceerman, S. and Bevan, M. V., Plant Cell Rep., 1988, 7, 13–16). From the obtained plants, chromosomal DNA was extracted, and the potato (MayQueen) transformants in which CYP2C19 was integrated into the chromosomes were selected by PCR using primers specifically annealing to human CYP2C19.

EXAMPLE 18

Confirmation of the Expression of the Target Enzyme in the Potato Transformants by Western Blot The microsomal protein (50 µg) was extracted from the potato transformants obtained in Example 17 and subjected to the SDS-polyacrylamide gel electrophoresis. The proteins in the gel were adsorbed onto PVDF membrane. The protein was detected using anti-CYP2C19 polyclonal antibody as a probe. As a result, the band reactive with the CYP2C19 antibody was detected at the position corresponding to about 58 kDa. It was confirmed that the target enzyme was produced in the potato transformants and localized in the chromosomal fraction.

EXAMPLE 19

Assay for Herbicide Resistance of Potato Transformants

The potato transformants and the non-transformed potato plants proliferated from axillary buds and rooted were transferred to pots filled with culture soil for vegetables, and either herbicide metolachlor or acetochlor was dispersed 1 week after transfer to measure degrees of death. As a result, as shown in Table 4, the transformant showed higher resistance compared with the non-transformed MayQueen.

Values in the table show the following condition.

1, alomost dead;

2, severely inhibited growth;

3, slightly inferior growth;

4, the same growth as that when herbicide was not dispersed.

TABLE 4

Resistance of the potato transformants 14 days after dispersal to herbicides

| | Metolachlor (µmol/pot) | | | Acetochlor (µmol/pot) | | |
|---|---|---|---|---|---|---|
| | 10 | 15 | 20 | 5 | 10 | 15 |
| MayQueen | 2 | 2 | 1.5 | 2 | 2 | 1 |
| Transformant | 2.5 | 3.5 | 2.5 | 3.5 | 3 | 2.5 |

EXAMPLE 20

Herbicide Metabolism in the Potato Transformants

The potato transformants proliferated from axillary buds, elongated to about 10 cm, were cultured in the medium added with the $^{14}$C-labeled pyributicarb at the concentration of 10 µM. The plants were cultured for 8 days, and metabolites were extracted from the plants (Murakami, M. et al., J. Pesticide. Sci., 1997, 22, 222–225). The metabolites and the culture solution were analyzed by thin layer chromatography (Shiota, N. et al., Pestic. Biochem. Physiol., 1996, 54, 190–198). As a result, the amounts of pyributicarb in transgenic plant and in the medium were obviously reduced compared with the amounts in the case of the non-transformed MayQueen.

EXAMPLE 21

Figure 4:
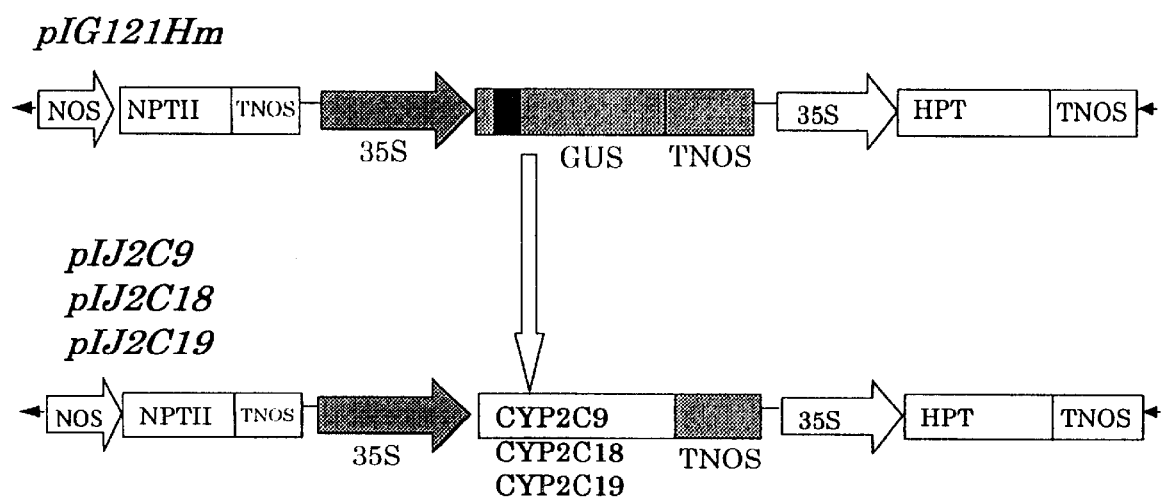
FIG. 4 schematically shows construction of binary plasmids pIJ2C9, pIJ2C18, and pIJ2C19. NOS, Nos promoter; NPT II, kanamycin resistance gene; TNOS, Nos terminator; 35S, cauliflower mosaic virus 35S promoter; HPT, hygromycin resistance gene; GUS, β-glucuronidase gene.

Construction of Binary Plasmids pIJ2C9, pIJ2C18, and pIJ2C19, Introduction into Agrobacterium, and Infection to Rice Plants FIG. 4 shows the constructed binary plasmids, pIJ2C9, pIJ2C18, and pIJ2C19. Human P4502C9, human P4502C18, and human P4502C19 genes excised with Xba I and Sac I were inserted into pBI121-derived binary vector pIG121Hm digested with Xba I and Sac I to construct the plasmid vectors pIJ2C9, pIJ2C18, and pIJ2C19, respectively, which was expressed by the cauliflower mosaic virus 35S promoter.

In the same manner as Example 2, the constructed binary plasmids pIJ2C9, pIJ2C18, and pIJ2C19 were introduced into the agrobacteria and the presence of the plasmids was confirmed.

In the same manner as Example 3, rice plants were infected with the agrobacterium.

EXAMPLE 22

Germination Assay for Herbicide Resistance of Human P4502C9 Gene-Introduced Rice R1 Seeds The transgenic rice plants (R0 individuals) were grown to obtain R1 seeds. The obtained R1 seeds were sowed on hormone-free Murashige & Skoog (MS) medium containing chlorosulfuron, which shows a weeding effects on gramineous plants, and tolerance at germination was examined. Four seeds threshed and sterilized with sodium hypochlorite solution were sowed on each 2 ml of MS solid medium containing chlorosulfuron at the final concentration of 250 nM. In the seeds of Nipponbare into which the gene was not introduced, germination was inhibited, and both shoots and roots did not elongate after about 4 to 7 days. On the other hand, in the seeds of transgenic rice plants, individuals in which shoots and roots normally elongated in the same manner as those elongated in herbicide-free medium were segregated. Table 5 shows the result.

EXAMPLE 23

Germination Assay for Herbicide Resistance of Human P4502C18 Gene-Introduced and Human P4502C19 Gene-Introduced Rice R1 Seeds The transgenic rice plants (R0 individuals) were grown to obtain R1 seeds. The obtained R1 seeds were sowed on hormone-free Murashige & Skoog (MS) medium containing metolachlor, which shows a weeding effect on gramineous plants, and tolerance at germination was examined. Four seeds threshed and sterilized with sodium hypochlorite solution were sowed on each 2 ml of MS solid medium containing metolachlor at the final concentration of 4 µM. In the seeds of Nipponbare into which the gene was not introduced, germination was inhibited, and both shoots and roots did not elongate after about 4 to 7 days. On the other hand, in the seeds of transgenic rice plants, individuals in which shoots and roots normally elongated in the same manner as those elongated in herbicide-free medium were segregated. Table 5 shows the result.

TABLE 5

Herbicide tolerance at the germination of the rice plants (R1 seed) into which various molecular species of P450 were introduced

| Molecular species | 2C9 | 2C18 | 2C19 |
| --- | --- | --- | --- |
| Herbicide Concentration · Amount | Chlorosulfuron 250 nM · 2 ml | Metolachlor 4 µM · 2 ml | Metolachlor 4 µM · 2 ml |
| The number of sample lines | 44 | 72 | 68 |
| The number of tolerant lines | 15 | 3 | 13 |

EXAMPLE 24

Metabolism of Various Herbicides in Microsomes of Each of Recombinant Yeast Strains Respectively Expressing One of 11 Human P450 Molecular Species To 0.1 M potassium phosphate buffer (pH 7.4), the microsomal fraction prepared from each of yeast strains respectively expressing one of 11 human P450 molecular species (obtained from Sumitomo Chemical) was added so that the amount of the p450 would be 25 pmol. Furthermore, 0.5 mM NADPH, 5 mM glucose 6 phosphate, 1 U/ml glucose 6 phosphate dehydrogenase, and 0.1 mM each of the following herbicides (those available in the market were used) were added at the final concentrations thereto to make the total volume of 100 µl. The reaction mixture was shaken at 37° C. for 60 min, and an organic solvent was added thereto for the extraction. The extract was applied to the high performance liquid chromatography, and the metabolite was measured. As a result, human CYP1A1, CYP2B6, and CYP2C19 were found to metabolize the following herbicides.

Human CYP1A1: atrazine, chlorotoluron, methabenzthiazuron, and norflurazon;

Human CYP2B6: acetochlor and metolachlor;

Human CYP2C19: acetochlor, atrazine, chlorotoluron, methabenzthiazuron, metolachlor, norflurazon, and pyributicarb.

EXAMPLE 25

Human P450 Molecular Species-Expression Plasmid

The following materials were used in the present Example. The human CYP1A1 cDNA was prepared from human cDNA libraries by synthesizing PCR primers designed based on the known sequences and by cloning by PCR. The human CYP2B6 cDNA of Example 1 was used. The human CYP2C19 cDNA of Example 15 was used. Anti-human CYP2B6antibody and anti-CYP2C9 antibody were gifts from Sumitomo chemical. Anti-rat CYP1A1 antibody was purchased from Daiichi Kagaku Kogyo. Plasmid B100 was a gift from Dr. Teruo Ishige, Minsistry of Agriculture, Forestry and Fisheries Research Council Secretariat. The plasmid pBI121 was purchased from Toyobo. Restriction enzymes, T4 DNA ligase, ligation kit, Sal I DNA linker, Xho I DNA linker, Klenow fragment, and alkaline phosphatase were purchased from Takara Shuzo. ISOPLANT and QuichPrep Micro mRNA Purification kit were purchased from Wako Pure Chemical Industries, Ltd. and Amersham Pharmacia Biotech, respectively. Herbicides acetochlor, atrazine, chlorotoluron, methabenzthiazuron, metolachlor, and norflurazon were purchased form Hayashi Jun-yaku Kogyo. Herbicide pyributicarb was provided by Dainippon Ink and Chemicals, Incorporated.

(1) Construction of plant expression vector pSNTLX

Figure 5:
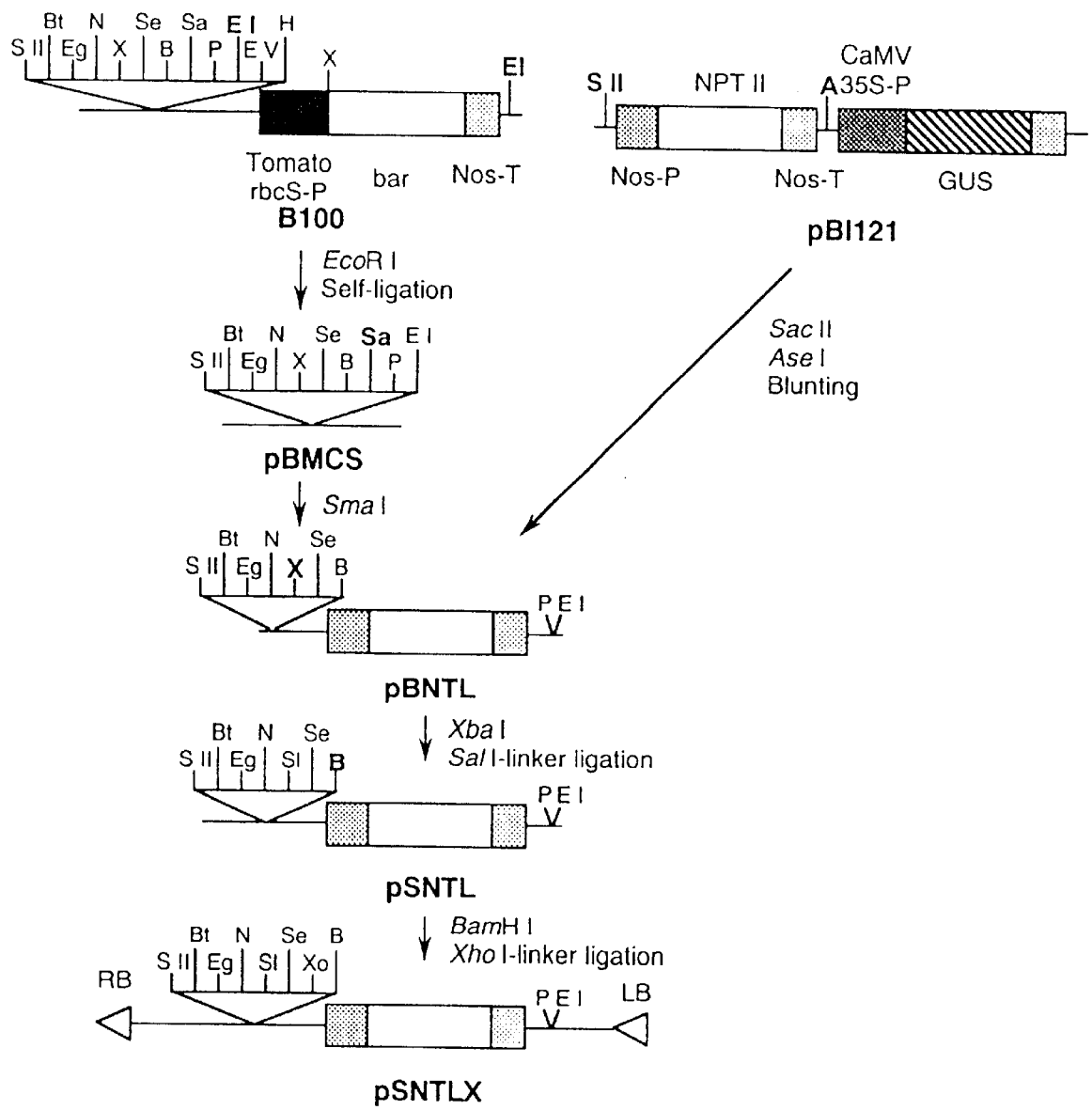
FIG. 5 shows a method for constructing plasmid vector pSNTLX. Symbols in the figure indicate as follows.
  rbcS-P, ribulose-bisphosphate carboxylase/oxygenase small subunit promoter;
  bar, the cording region of phosphinothricin acetyltransferase;
  Nos-T, Nopaline synthetase terminator;
  Nos-P, Nopaline synthetase promoter;
  NPT II, the cording region of neomycin phosphotransferase II;
  CaMV 35S-P, cauliflower mosaic virus 35S promoter;
  GUS, the cording region of β-glucuronidase;
  S II, cleavage site for restriction enzyme Sac II;
  Bt, cleavage site for restriction enzyme BStX I;
  Eg, cleavage site for restriction enzyme Eag I;
  N, cleavage site for restriction enzyme Not I;
  X, cleavage site for restriction enzyme Xba I;
  Se, cleavage site for restriction enzyme Spe I;
  B, cleavage site for restriction enzyme BamH I;
  Sa, cleavage site for restriction enzyme Sma I;
  P, cleavage site for restriction enzyme Pst I;
  E I, cleavage site for restriction enzyme EcoR I;
  E V, cleavage site for restriction enzyme EcoR V;
  H, cleavage site for restriction enzyme Hind III;
  A, cleavage site for restriction enzyme Ase I;
  Sl, cleavage site for restriction enzyme Sal I;
  Xo, cleavage site for restriction enzyme Xho I.

Plant expression vector pSNTLX was constructed using B100 plasmid and pBI121 plasmid as shown in FIG. 5. The target gene-introduced individuals can be obtained with high possibility by using this vector due to NPT II expression unit at the LB side in this vector. Moreover this vector comprises a multicloning site capable of introducing more than one type of P450 cDNA in various combinations. Following is the construction procedure.

First, B100 vector was digested with EcoR I and self-ligated at the cleaved sites to construct pBMCS. This vector was further digested with Sma I. pBI121 vector was digested with Sac II and Ase I, and the obtained fragment was blunt-ended and inserted into the Sma I-digested pBMCS to obtain pBNTL. pBNTL was digested with Xba I, blunt-ended using the Klenow fragment, and dephosphorylated with alkaline phosphatase. Sal I linkers were inserted there-into and ligated. pSNTL vector thus constructed was digested with BamH I and ligated with the Xho I linkers in the same manner to obtain pSNTLX vector.

(2) Construction of plant expression plasmid pIKBAC for human CYP1A1, CYP2B6, and CYP2C19

Figure 6:
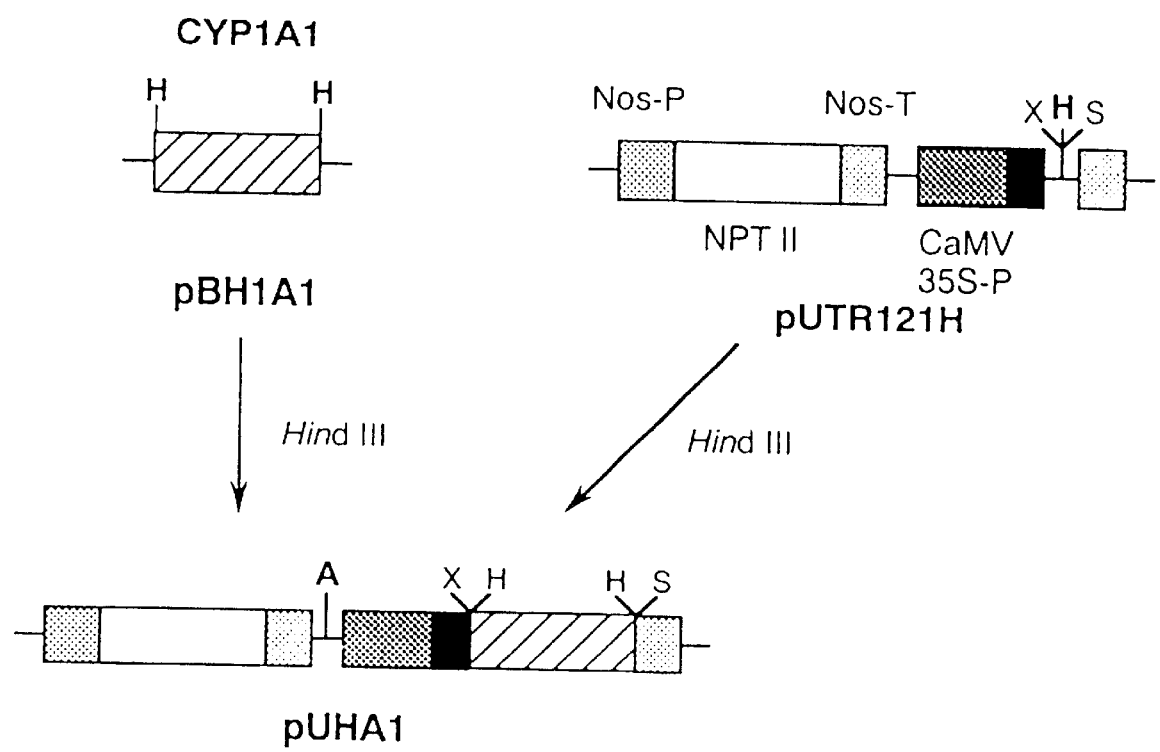
FIG. 6 shows a method for constructing human CYP1A1 expression plasmid pUHA1. A black box and a box with diagonal lines (thin lines) in the figure indicate 5' non-translational region of alfalfa mosaic virus, and a coding region of human CYP1A1, respectively.
Figure 7:
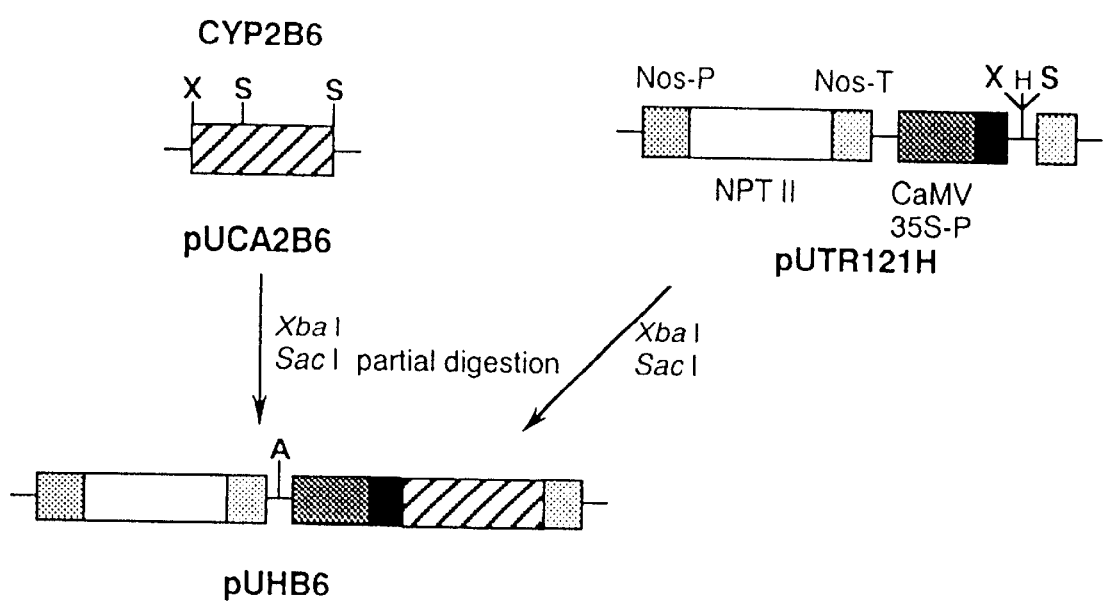
FIG. 7 shows a method for constructing human CYP2B6 expression plasmid pUHB6. A box with diagonal lines in the figure indicates a coding region of human CYP2B6.

First, expression plasmids puHA1 shown in FIG. 6 and pUHB6 shown in FIG. 7 were constructed. Then, pSXA1 and pSSA1 shown in FIG. 8, pXXB6 shown in FIG. 9, and pSSC19 shown in FIG. 10 were further constructed to construct the plasmid pIKBAC shown in FIG. 11.

(2-1) Construction of plasmid pUHA1 for expressing human CYP1A1

To the pUTR121H vector digested with Hind III, the fragment containing human CYP1A1 cDNA obtained by digesting the pBH1A1 with Hind III was inserted as shown in FIG. 6 to obtain pUH1A1.

(2-2) Construction of plasmid pUHB6 for expressing human CYP2B6

To vector pUTR121H digested with Xba I and Sac I, the fragment containing human CYP2B6 cDNA obtained by partially digesting pUCA2B6 with Xba I and Sac I was inserted as shown in FIG. 7 to construct pURB6.

(2-3) Construction of plasmid simultaneously expressing three types of human CYP1A1, CYP2B6, and CYP2C19

Figure 8:
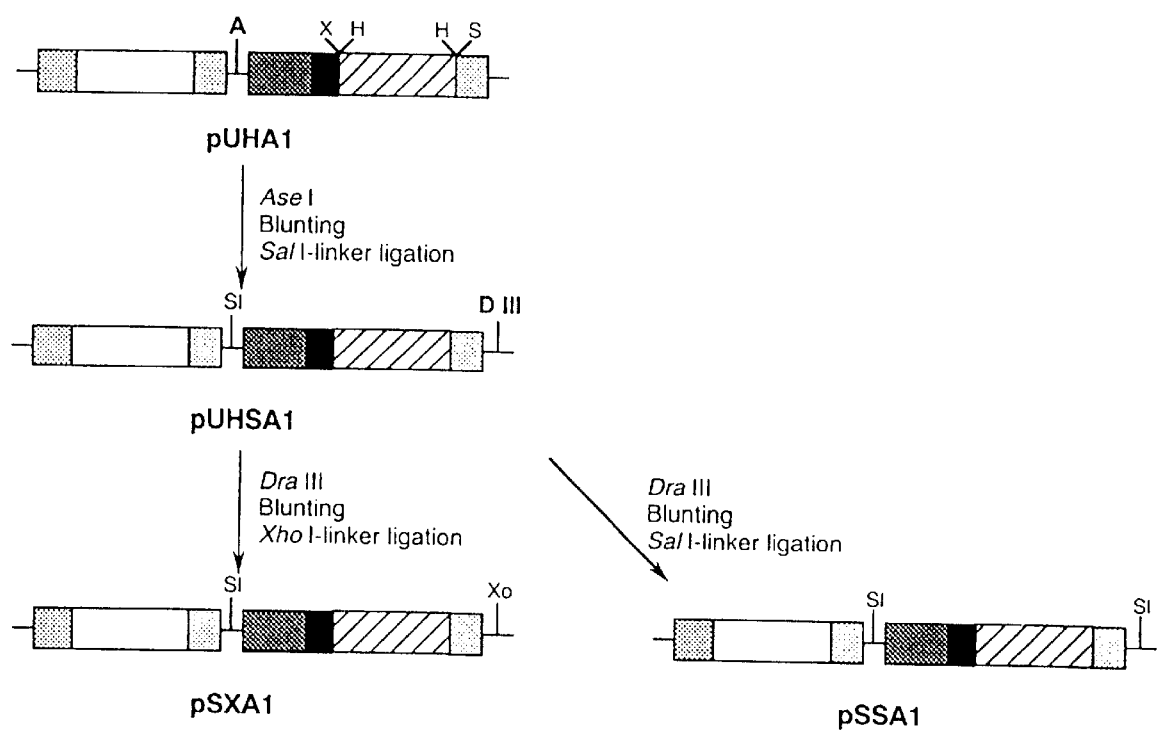
FIG. 8 shows a method for constructing plasmids pSXA1 and pSSA1. "D III" in the figure indicates a cleavage site for restriction enzyme Dra III.

As shown in FIG. 8, for constructing pSXA1 and pSSA1, pUHA1 was treated with Ase I and blunt-ended using the Klenow fragment, and Sal I linkers were inserted and ligated. pUHSA1 obtained was digested with Dra III in the same manner, and new restriction sites were created using Xho I linkers to make pSXA1. pSSA1 was prepared using Xho I linker after the digestion with Dra III in the same manner.

Figure 9:
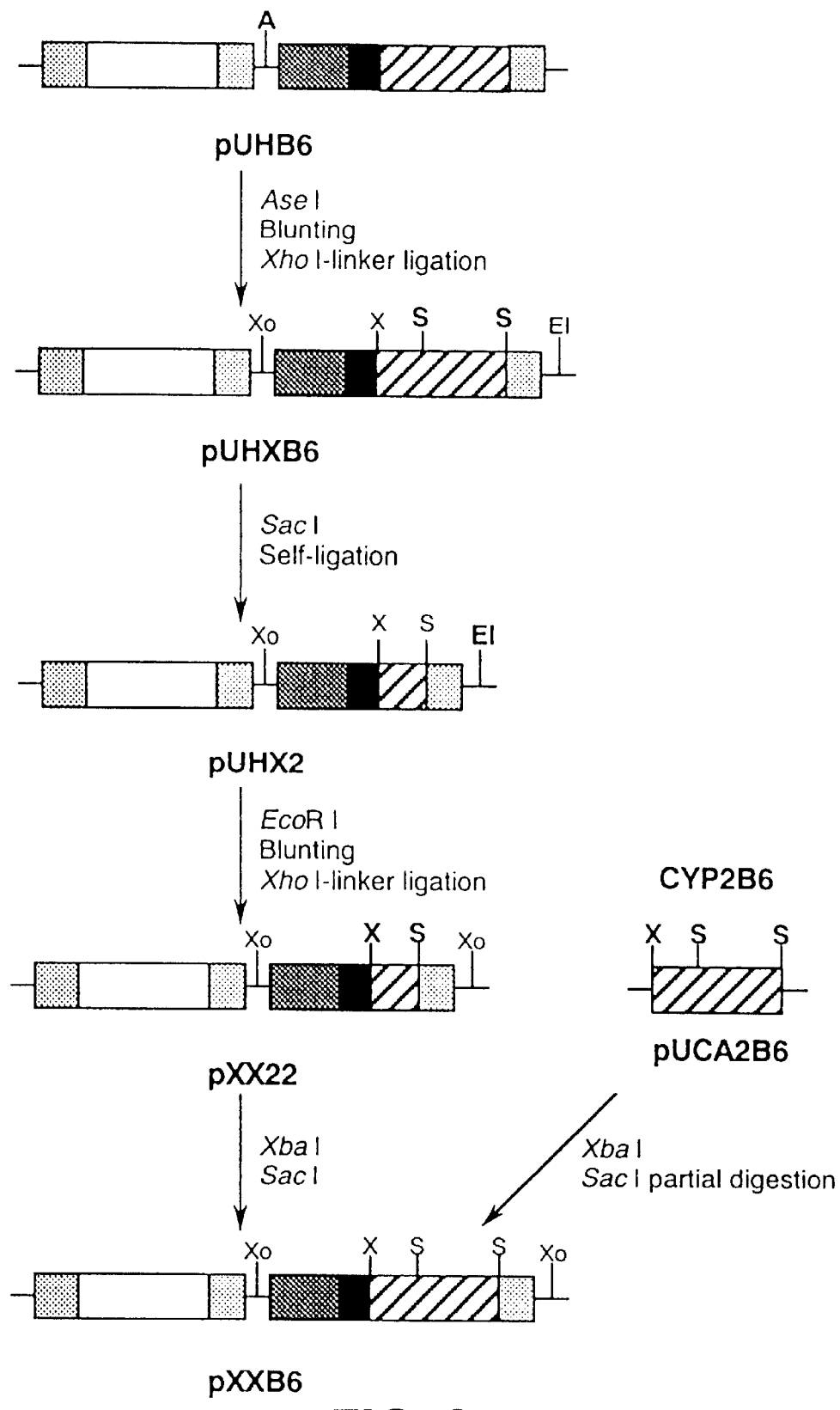
FIG. 9 shows a method for constructing plasmid pXXB6.

As shown in FIG. 9, for constructing pXXB6, pUHXB6 was obtained by treating pUHB6 with Ase I, blunt-ending, and inserting Xho I linker. Then, for digesting at the EcoR I site close to the terminator of CYP2B6 gene, CYP2B6 cDNA was digested at an interior Sac I site and self-ligated. pUHX2 obtained was completely digested with EcoR I, blunt-ended, and ligated with the Xho I linker. pXX22 obtained was digested at the Xba I and Sac I sites and ligated with pUCA2B6 partially digested with Xba I and Sac I to obtain pXXB6.

Figure 10:
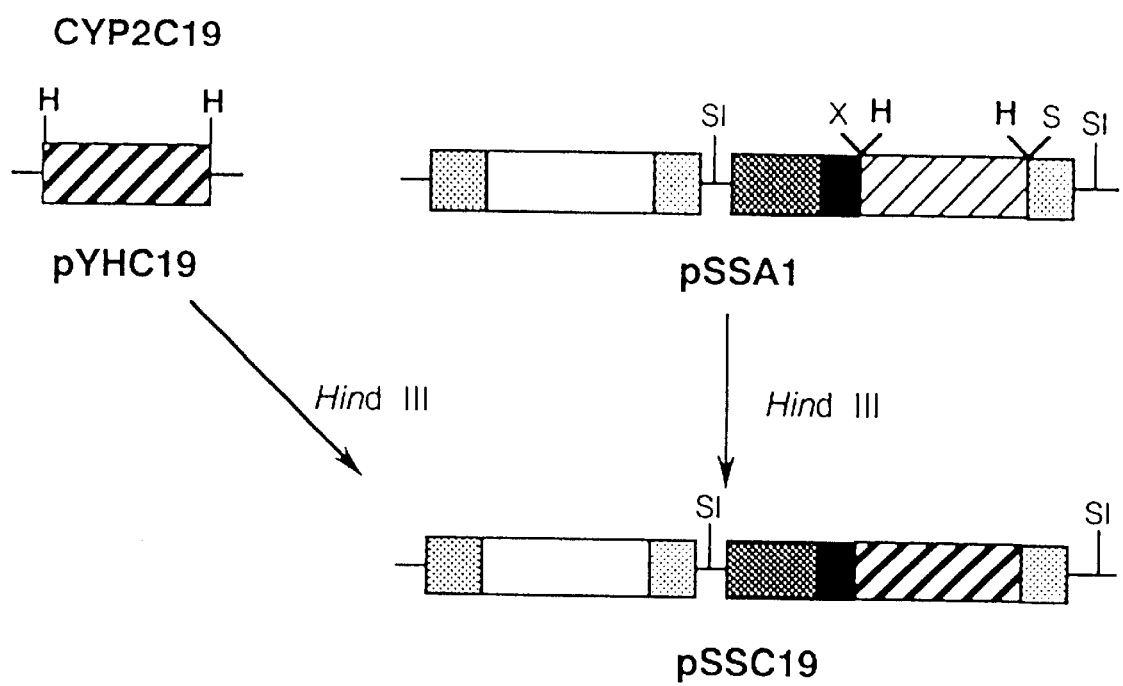
FIG. 10 shows a method for constructing plasmid pSSC19.

As shown in FIG. 10, to construct pSSC19, the fragment containing human CYP2C19 cDNA obtained by digesting pYHC19 with Hind III was inserted into the vector fragment of Hind III-digested pSSA1, which was constructed in FIG. 8.

(2-4) Construction of pIKBAC

Figure 11:
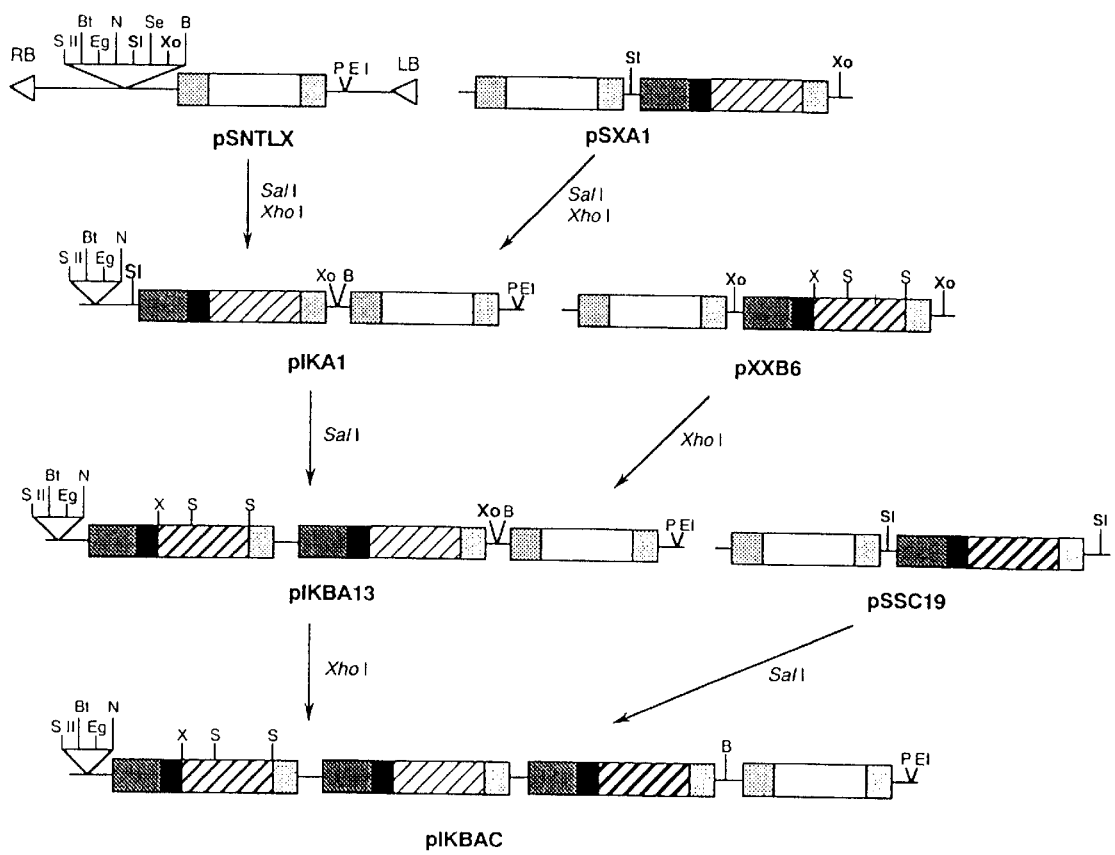
FIG. 11 shows a method for constructing human CYP1A1, CYP2B6, and CYP2C19 expression plasmid pIK-BAC.

As shown in FIG. 11, pIKA1 was obtained by ligating the 12-kb Sal I-Xho I fragment of PSNTLX with the 3.2-kb Sal I-Xho I fragment of pSXA1. pIKA1 was digested with Sal I and ligated with the 2.8-kb Xho I fragment of pXXB6 in the same manner to obtain pIKBA13. The pIKBAC was obtained by ligating the 3.8-kb Sal I fragment of pSSC19 with pIKBA13 vector treated with Xho I.

EXAMPLE 26

Plant Transformation

Each of the plant expression plasmids prKBAC, pUHA1, pUHB6, and puHC19 (refer to Example 15) was introduced into *Agrobacterium tumefaciens* strain LBA4404 by electroporation method.

Plants were infected with Agrobacterium using microtubers of sterilely cultured potato, *Solanum tuberosum* cv. MayQueen. The microtubers were prepared by culturing plants under light exposure in 5 ml liquid medium containing 2% sucrose at 20° C. for 2 weeks, then adding 6.5 ml of liquid medium containing 15% sucrose thereto, and culturing in the dark at 18° C. for 1.5 to 2 months. The microtubers were sliced, peeled, and immersed in the Agrobacterium liquid. The slices were cultured on IS1 medium for 3 days, and the microtubers infected with Agrobacterium harboring the plasmid were cultured on IS2 medium containing antibiotics, 100 mg/l kanamycin and 300 mg/l cefotaxime for 2 to 3 months. Shoots reproduced from the calli were transplanted on IS15 medium containing 100 mg/l kanamycin and 200 mg/l cefotaxime, and rooting was confirmed. Regenerated plants with roots were considered as the kanamycin resistant individuals.

EXAMPLE 27

Selection of Transformants Highly Expressing P450

For selecting transformants highly expressing P450, 7-ethoxycoumarin O-deethylation activity using 7-ethoxycoumarin, which is a standard substrate for drug-metabolizing P450, and Western blot analysis using microsomal fractions was conducted. In order to confirm the expression of introduced P450 gene, Southern blot analysis and Northern blot analysis were conducted.

(1) Selection by 7-ethoxycoumarin O-deethylation activity

Leaves of the kanamycin-resistant individuals (0.1 g) were cultured in 5 ml of a liquid medium containing 2% sucrose with 100 µl of 20 mM 7-ethoxycoumarin for 3 days. Then, the leaves were crushed in 500 µl of 0.1 M potassium phosphate buffer (pH 7.4), and chloroform was added to the supernatant and mixed. To the chloroform layer, 0.01 N NaOH/0.1 M NaCl was added, and measurement was performed at excitation wavelength of 366 nm and at emission of 452 nm with the Hitachi fluorometer. As a result, individuals, T1977 and T1979, expressing three types of P450 simultaneously were selected and these showed higher activity than the control. Each of CYP1A1-expressing individual S1965, and CYP2B6-expressing individual S1972 was selected in the same manner.

(2) Selection by Western blot analysis using microsomal fraction

A microsomal fraction was prepared from plants by the method of Shiota et al. (Plant Physiology, 1994, 106, 17–23). Twenty micrograms of microsomal fractions were subjected to the SDS-polyacrylamide gel electrophoresis and transferred onto a nitrocellulose membrane. To specifically detect P450 protein, each of anti-rat CYP1A1 antibody, anti-human CYP2B6 antibody, and anti-human CYP2C9 antibody (anti-human CYP2C9 antibody reacts with human CYP2C19) described in Example 25 was used as a primary antibody. For a secondary antibody, anti-goat IgG-alkaline phosphatase antibody and anti-rabbit IgG-alkaline phosphatase antibody purchased from Sigma were used.

Figure 12A:
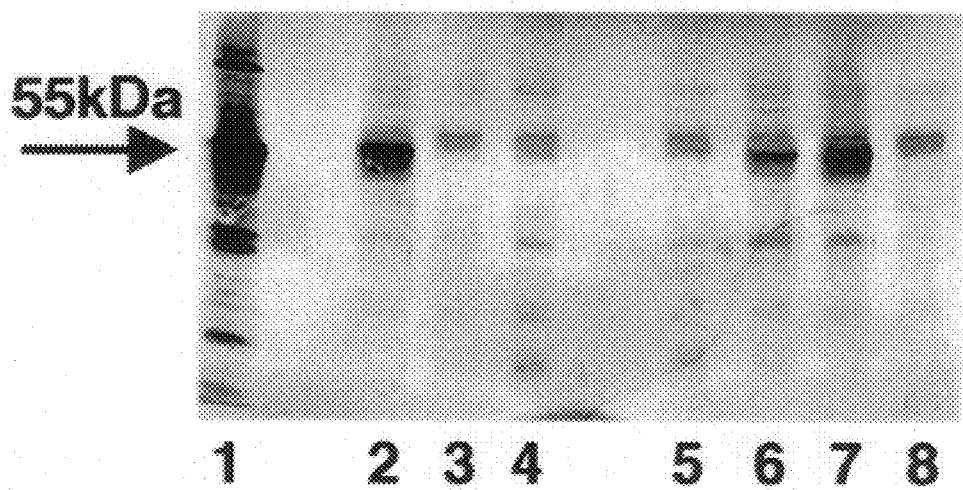
FIG. 12 shows western blot analyses for microsomal fractions of transformants.
Figure 12B:
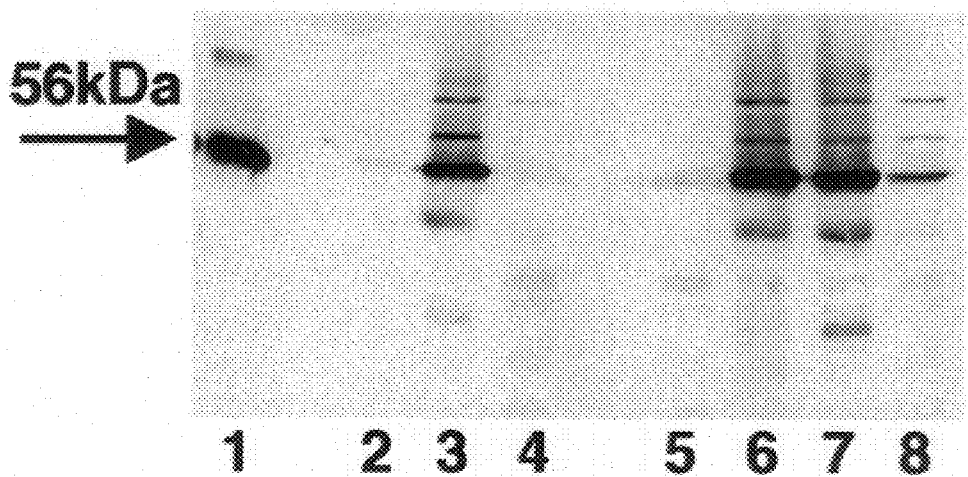
Figure 12C:
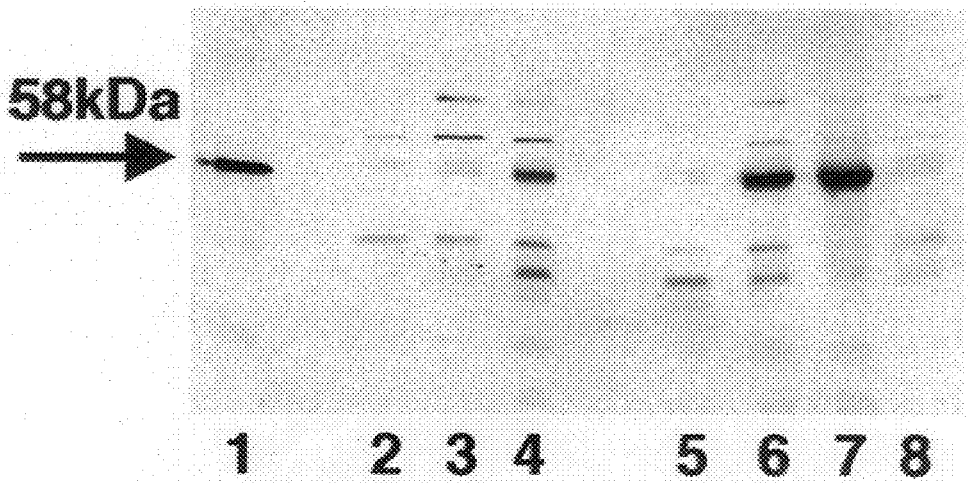

As a result, using any antibodies, the bands for the proteins corresponding to human CYP1A1, human CYP2B6, and human CYP2C19 were confirmed. These results revealed that three types of P450 proteins were synthesized in the plants. Because more P450 proteins were accumulated in T1977 plant, this was used to the following experiment. Similarly, CYP2C19 expressing individual, S1974, was selected. FIG. 12 shows the results.

(3) Measurement of 7-ethoxyresorufin O-deethylation activity using a microsomal fraction A reaction was initiated by adding 7-ethoxyresorufin to the concentration of 10 $\mu$M to a reaction solution containing 0.1 M potassium phosphate buffer (pH 7.4), 3 mM NADPH, and 1 mg/ml microsomal fractions at the final concentrations. The mixture was incubated at 37° C. for 30 min, ice-cooled acetone was added thereto, and allowed to stand on ice for 10 min. The supernatant was measured using the fluorometer (excitation wavelength of 550 nm, and emission of 586 nm).

As a result, T1977 and S1965 showed activity about 27 and 53 times higher, respectively, than the controls. These results indicate that human CYP1A1 was functionally expressed in T1977 and S1965. Inhibition of activity by addition of carbon monoxide and absence of NADPH indicated P450-dependency. On the other hand, an increased activity was not observed in S1972 or S1974. Table 6 shows these results. In the table, "EROD activity" of (a) indicates 7-ethoxyresorufin O-deethylase activity (pmol/min/mg of protein) and means±standard deviations in three independent experiments. In (b), the values indicate the activities in the presence of carbon monoxide. In (c), the values indicate the activities in the absence of NADPH. (d) indicates that no measurement was performed.

TABLE 6

7-ethoxyresorufin O-deethylase (EROD) activity

| Transgenic plants | EROD activity[a] | CO (Inhibition rate)[b] | -NADPH (Inhibition rate)[c] |
|---|---|---|---|
| Control | 0.11 ± 0.01 | 0.06 (45%) | 0.02 (82%) |
| T1977 | 2.92 ± 0.72 | 0.69 (76%) | 0.02 (99%) |
| S1965 | 5.78 ± 0.51 | 1.33 (77%) | 0.06 (99%) |
| S1972 | 0.12 ± 0.03 | —[d] | — |
| S1974 | 0.14 ± 0.03 | — | — |

(4) Southern blot analysis using genomic DNA

Genomic DNA was prepared from plants by ISOPLANT. Southern blot analysis was conducted by the method of Inui et al. (Breeding Science, 1998, 48 (2), 135–143).

As a result, in the genomic DNA of T1977, all probes of CYP1A1, CYP2B6, and CYP2C19 were reacted, and bands were detected. Thus, the insertion of all these three types of P450 cDNA into genomic DNA was shown. In addition, insertion of each cDNA was similarly confirmed in S1965, S1972, and S1974. FIG. 13 shows the results.

(5) Northern blot analysis using mRNA mRNA was prepared from plants using QuickPrep Micro mRNA Purification kit. Northern blot analysis was conducted by the method of Inui et al. (Breeding Science, 1998, 48 (2), 135–143).

As a result, in T1977, the bands corresponding to three types of P450 mRNA were detected. In addition, in S1965, S1972, and S1974, transcription to each mRNA was similarly confirmed. FIG. 14 shows the result.

EXAMPLE 28

Herbicide Tolerance Assay for Transformants

Transformants grown under sterile conditions were transferred to a pot, accustomed for 1 week, and further cultured for 1 week. Then, herbicides were dispersed. The plants were grown at 20° C. under 8-hour day light conditions. Photosynthesis inhibition herbicides, atrazine (1.2 $\mu$mol), chlorotoluron (17.6 $\mu$mol), and methabenzthiazuron (10 $\mu$mol) wee dispersed. Protein synthesis-inhibiting herbicides, acetochlor (20 $\mu$mol) and metolachlor (30 $\mu$mol) were dispersed. Carotenoid biosynthesis-inhibiting herbicide norflurazon (12 $\mu$mol) was dispersed. Lipid biosynthesis-inhibition herbicide pyributicarb (20 $\mu$M) was added to the medium.

As a result, T1977 showed strong resistance to the all herbicides. S1965 showed strong resistance to atrazine, chlorotoluron, methabenzthiazuron, and norflurazon; S1972 to acetochlor and metolachlor; and S1974 to acetochlor, atrazine, and metolachlor. FIGS. 15, 16, 17, and 18 show these results.

INDUSTRIAL APPLICABILITY

Transgenic plants into which P450 genes or fusion enzyme genes with a P450 reductase genes of the present invention have been introduced are capable of metabolizing drug including agrochemicals, for example herbicides. Therefore, in the agricultural fields, crop yield can be increased using these herbicide-tolerant plants in combination with various herbicides. Moreover, these plants were safe for humans and livestock which eat these plants since these plants can metabolize and detoxify agrochemicals, for example, herbicides, insecticides, and fungicide in plants. In addition, these plants are extremely environment-friendly, because absorbing and decomposing toxic substances dispersed in the soil, for example, agrochemicals, such as herbicides, or others. Thus, the plants are useful as a plant for phytoremediation.

What is claimed is:

1. A transgenic plant comprising a plant cell harboring a DNA molecule comprising in operable linkage:
    (a) a promoter which functions in plant cells;
    (b) more than one P450 monooxygenase gene belonging to the CYP2 family wherein said P450 monooxygenase gene is selected from the group consisting of the CYP2B6 gene, the CYP2C9 gene, the CYP2C18 gene, and the CYP2C19 gene;
    (c) a terminator which functions in plants cells; and
    (d) a P450 reductase gene;
whereby the transgenic plant can decompose a foreign compound by the oxidative metabolism.

2. The transgenic plant of claim 1, wherein the transgenic plant is a gramineous plant or a solanaceous plant.

3. The transgenic plant of claim 1, wherein a foreign compound is an environmental load or an extrinsic endocrine disruptor.

4. The transgenic plant of claim 1, wherein the transgenic plant has herbicide tolerance.

5. A propagation material of the plant of claim 1, which propagation material comprises said DNA molecule.

6. A method for removing a foreign compound in the environment, comprising contacting the foreign compound with the transgenic plant of claim 1.

7. The method of claim 6, wherein the foreign compound is an environmental load or an extrinsic endocrine disruptor.

8. The transgenic plant of claim 1, wherein the foreign compound is a herbicide selected from the group consisting of a triazine compound, a urea compound, a diazine compound, a pyrimidinyloxybenzene compound, an acetanilide compound, a dinitroaniline compound, a benzofuranylalkanesulfonate compound, a sulfonylurea compound, and a carbamate compound.

9. The method of claim 6, wherein the foreign compound is a herbicide selected from the group consisting of a triazine compound, a urea compound, a diazine compound, a pyrimidinyloxybenzene compound, an acetanilide compound, a dinitroaniline compound, a benzofuranylalkanesulfonate compound, a sulfonylurea compound, and a carbamate compound.

* * * * *

UNITED STATES PATENT AND TRADEMARK OFFICE
CERTIFICATE OF CORRECTION

PATENT NO.   : 6,613,961 B1
DATED        : September 2, 2003
INVENTOR(S)  : Hideo Ohkawa et al.

It is certified that error appears in the above-identified patent and that said Letters Patent is hereby corrected as shown below:

Title page,
Item [56], References Cited, OTHER PUBLICATIONS, "Inui, H. et al.", reference, "Xenobiotic-MetabolizinogHuman" should read -- Xenobiotic-Metabolizing Human --.

Column 1,
Line 46, "enzymegenes" should read -- enzyme genes --.

Column 19,
Line 47, "pURB6" should read -- pUHB6 --.

Column 20,
Line 19, "prKBAC" should read -- PIKBAC --.

Signed and Sealed this

Eleventh Day of November, 2003

JAMES E. ROGAN
*Director of the United States Patent and Trademark Office*